United States Patent [19]

Sucrow et al.

[11] Patent Number: 4,943,384
[45] Date of Patent: Jul. 24, 1990

[54] CYCLOHEXANE DERIVATIVES

[75] Inventors: Wolfgang Sucrow, Paderborn; Herbert Wolter, Paderborn-Barkhausen; Rudolf Eidenschink, Munster, all of Fed. Rep. of Germany

[73] Assignee: Merck Patent Gesellschaft mit Beschränkter Haftung, Darmstadt, Fed. Rep. of Germany

[21] Appl. No.: 2,596

[22] Filed: Nov. 21, 1986

[30] Foreign Application Priority Data

Mar. 22, 1985 [DE] Fed. Rep. of Germany ....... 3510434
Mar. 18, 1986 [WO] PCT Int'l Appl. ... PCT/EP86/00156

[51] Int. Cl.⁵ ........................ G02F 1/13; C09K 19/34; C09K 19/30; C09K 19/06
[52] U.S. Cl. ............................ 252/299.61; 252/299.5; 252/299.6; 252/299.62; 252/299.63; 252/299.64; 252/299.65; 252/299.66; 252/266.67; 350/350 R; 350/350 S; 544/298; 544/339; 544/335; 549/372; 549/373; 549/374; 549/375; 558/414; 558/415; 558/416; 558/426; 558/428; 558/430; 558/431; 560/59; 560/73; 560/102; 560/106; 560/107; 560/108; 560/109; 560/118; 560/126; 568/303; 568/325; 568/326; 568/327; 568/328; 568/329; 568/368; 568/374
[58] Field of Search ...................... 252/299.61, 299.63, 252/299.5, 299.62, 299.65, 299.66, 299.67, 299.68, 299.6; 350/350 R, 350 S

[56] References Cited

U.S. PATENT DOCUMENTS

| | | | |
|---|---|---|---|
| 4,406,814 | 9/1983 | Ferrato | 252/299.63 |
| 4,422,951 | 12/1983 | Sagimori et al. | 252/299.63 |
| 4,434,073 | 2/1984 | Sucron et al. | 252/299.63 |
| 4,510,069 | 4/1985 | Eidenschink et al. | 252/299.63 |
| 4,534,883 | 8/1985 | Sugimori et al. | 252/299.63 |
| 4,629,581 | 12/1986 | Boller et al. | 252/299.63 |
| 4,659,499 | 4/1987 | Ferrato | 252/299.63 |
| 4,663,073 | 5/1987 | Sucrow et al. | 252/299.63 |
| 4,698,177 | 10/1987 | Tanaka et al. | 252/299.63 |
| 4,704,227 | 11/1987 | Krause et al. | 252/299.61 |
| 4,707,295 | 11/1987 | Pohl et al. | 252/299.61 |
| 4,715,984 | 12/1987 | Krause et al. | 252/299.61 |

FOREIGN PATENT DOCUMENTS

| | | | |
|---|---|---|---|
| 117476 | 9/1984 | European Pat. Off. | 252/299.61 |
| 61-268646 | 11/1986 | Japan | 252/299.63 |
| 62-185036 | 8/1987 | Japan | 252/299.63 |

OTHER PUBLICATIONS

Cereghetti, M. et al., Helv. Chim. Acta., vol. 65, No. 4, pp. 1318-1331 (1982).
Demus, D., et al., Flussige Kristalle in Tabellen, Veb Deutscher Verlag fur Grundstoffindustrie, Leipzig, pp. 38-43 (1974).
Sucrow, W., et al., Chem. Ber., vol. 119, pp. 387-406 (2/1982).
CA 65-18466h.
CA 53-7048b.

*Primary Examiner*—Teddy S. Gron
*Attorney, Agent, or Firm*—Millen & White

[57] ABSTRACT

Cyclohexane derivatives of the formula I

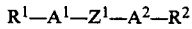

$$R^1-A^1-Z^1-A^2-R^2 \qquad \text{I}$$

wherein $R^1$ and $R^2$ are each H or an alkyl group which has 1-10 C atoms and in which one or two non-adjacent $CH_2$ groups can also be replaced by 0 atoms and/or —CO—groups, and/or —CO—O— groups and/or —CH=CH— groups, or are F, Cl, Br, CN or $R^3-A^3-Z^2-$, $A^1$ is —A—, $A^4-Z^o-A-$ or $-A-Z^o-A^4-$, A is a trans-1,4-cyclohexylene or 1,4-cyclohexenylene group which is unsubstituted or is monosubstituted or polysubstituted in the 2-, 3-, 5- and/or 6-position by F and/or Cl and/or Br and/or CN and/or an alkyl group or a fluorinated alkyl group each of which has 1-10 C atoms and in which one or two non-adjacent $CH_2$ groups can also be replaced by 0 atoms and/or —CO— groups and/or —CO—O— groups, which trans-1,4-cyclohexylene or 1,4-cyclohexenylene group can optionally also be substituted in the 1-position and/or 4-position and one or two $CH_2$ groups therein are replaced by —CO—, or $R^1-A^1-$ is a cyclohexyl group which is substituted in the 3-position by an alkyl group which has 1-10 C atoms and in which one or two non-adjacent $CH_2$ groups can also be replaced by 0 atoms and/or —CO— groups and/or —CO—O— groups and/or —CH=CH— groups, or is substituted in the 3-position by CN, in which cyclohexyl group one or two nonadjacent $CH_2$ groups can also be replaced by —O— or —CO—, $A^2$, $A^3$ and $A^4$ are each 1,4-phenylene which is unsubstituted or substituted by one or two F and/or Cl atoms and/or $CH_3$ groups and/or CN groups and in which one or two CH groups can also be replaced by N atoms and/or NO, or are 1,4-cyclohexylene wherein one or two non-adjacent $CH_2$ groups can also be replaced by 0 atoms, or are 1,3-dithiane-2,5-diyl, piperidine-1,4-diyl, 1,4-bicyclo(2,2,2)-octylene, decahydronaphthalene-2,6-diyl or 1,2,3,4-tetrahydronaphthalene-2,6-diyl groups or are —A—, $Z^o$, $Z^1$ and $Z^2$ are each —CO—O—, —O—CO—, —$CH_2CH_2$—, —$OCH_2$—, —$CH_2O$—, —$CH_2CO$—, —$COCH_2$—, —$CH_2CHCN$—, —$CHCNCH_2$— or a single bond, and $R^3$ is H or an alkyl group which has 1-10 C atoms and in which one or two non-adjacent $CH_2$ groups can also be replaced by 0 atoms and/or —CO— groups and/or —CO—O— groups and/or —CH=CH— groups, or is F, Cl, Br or CN, are suitable for use as components of liquid-crystal phases.

16 Claims, No Drawings

CYCLOHEXANE DERIVATIVES

The invention relates to cyclohexane derivatives of the formula I $$R^1-A^1-Z^1-A^2-R^2$$

wherein $R^1$ and $R^2$ are each H or an alkyl group which has 1-10 C atoms and in which one or two non-adjacent $CH_2$ groups can also be replaced by 0 atoms and/or —CO—groups and/or —CO—O— groups and/or —CH=CH— groups, or are F, Cl, Br, CN or $R^3-A^3-Z^2-$, $A^1$ is —A—, $A^4-Z^o-A-$ or $-A-Z_o-A^4-$, A is a trans-1,4-cyclohexylene or 1,4-cyclohexenylene group which is unsubstituted or is monosubstituted or polysubstituted in the 2-, 3-, 5- and/or 6-position by F and/or Cl and/or Br and/or CN and/or an alkyl group or a fluorinated alkyl group each of which has 1-10 C atoms and in which one or two non-adjacent $CH_2$ groups can also be replaced by 0 atoms and/or —CO— groups and/or —CO—O—groups, which trans-1,4-cyclohexylene or 1,4-cyclohexenylene group can optionally also be substituted in the 1-position and/or 4-position and one or two $CH_2$ groups therein can be replaced by —CO—, or $R^1-A^1-$ is a cyclohexyl group which is substituted in the 3-position by an alkyl group which has 1-10 C atoms and in which one or two non-adjacent $CH_2$ groups can also be replaced by 0 atoms and/or —CO— groups and/or —CO—O— groups and/or —CH=CH— groups, or is substituted in the 3-position by CN, in which cyclohexyl group one or two non-adjacent $CH_2$ groups can also be replaced by —O— or —CO—, $A^2$, $A^3$ and $A^4$ are each 1,4-phenylene which is unsubstituted or substituted by one or two F and/or Cl atoms and/or $CH_3$ groups and/or CN groups and in which one or two CH groups can also be replaced by N atoms and/or NO, or are 1,4-cyclohexylene wherein one or two non-adjacent $CH_2$ groups can also be replaced by 0 atoms, or are 1,3-dithiane- 2,5-diyl, piperidine-1,4-diyl, 1,4-bicyclo(2,2,2)-octylene, decahydronaphthalene-2,6-diyl or 1,2,3,4-tetrahydronaphthalene-2,6-diyl groups or are —A—, $Z^0$, $Z^1$ and $Z^2$ are each —CO—O—, —O—CO—, —$CH_2CH_2$—, —$OCH_2$—, —$CH_2O$—, —$CH_2CO$—, —$COCH_2$—, —$CH_2$—CHCN—, —$CHCNCH_2$— or a single bond, and $R_3$ is H or an alkyl group which has 1-10 C atoms and in which one or two non-adjacent $CH_2$ groups can also be replaced by 0 atoms and/or —CO— groups and/or —CO—O— groups and/or —CH=CH— groups, or is F, Cl, Br or CN.

In the following text, for the sake of simplicity, Ph is a 1,4-phenylene group, in which also one or more CH groups can be replaced by N and which, if appropriate, can also be laterally substituted by fluorin, Phe is a 1,4-phenylene group, Cy is a 1,4-cyclohexylene group, Dio is a 1,3-dioxane-2,5-diyl group, Bi is a bicyclo-(2,2,2)octylene group, Pip is a piperidine-1,4-diyl group, Pyr is a pyrimidine-2,5-diyl group, Pyn is a pyridazine-3,6-diyl group which can optionally also be in the form of the N-oxide, Dit is a 1,3-dithiane-2,5-diyl group and Dec is a decahydronaphthalene-2,6-diyl group.

Similar compounds are disclosed, for example, in German Patent Specification No. 2,636,684. In contrast with the present compounds, however, the compounds indicated therein contain no 1,3-disubstituted cyclohexane rings or cyclohexapone rings.

Like similar compounds, the compounds of the formula I can be used as components of liquid-crystal dielectrics, in particular for displays based on the principle of the twisted cell, the guest-host effect, the effect of the deformation of aligned phases, the SSFLC technology principle (U.S. Pat. No. 4,367,924) or the effect of dynamic scattering.

The invention was based on the object of finding new, stable liquid-crystal or mesogenic compounds suitable for use as components of liquid-crystal phases.

It has been found that the compounds of the formula I are excellently suitable for use as components of liquid-crystal phases. In particular, they make it possible to prepare stable liquid-crystal phases having a low value for the ratio $\Delta\epsilon/\epsilon_1$, which is advantageous for time division multiplexing, a high dissolving power for pleochroic dyestuffs, a very low optical anisotropy and a comparatively low viscosity. They also make it possible to prepare stable, chirally tilted smectic liquid-crystal phase of negative dielectric anisotropy, which allow the required planar orientation by superposition of an AC holding field of small amplitude on the driving field (J. M. Geary, SID meeting, Orlando/Florida, April/May 1985, Paper 8.3).

It has also been found that the compounds of the formula I are outstandingly suitable as components of chirally tilted, smectic liquid-crystal phases. Especially, they make it possible to prepare chemically particularly stable, chirally tilted smectic liquid-crystal phases with favorable ferro-electric phase regions, in particular with broad Sc* phase regions, negative or positive dielectric anisotropy, low optical anisotropy, favorable pitch level and, for such phases, high values for spontaneous polarization. P is the spontaneous polarization in $nC/cm^2$.

In addition, the range of liquid-crystal substances suitable from various aspects of technical performance in use for the preparation of liquid-crystal mixtures is, very generally, considerably broadened by the provision of the compounds of the formula I.

The compounds of the formula I possess a wide field of use. Depending on the selection of the substituents, these compounds can be used as the base materials of which liquid-crystal phases are predominantly composed; it is also possible, however, to add compounds of the formula I to liquid-crystal base materials consisting of other classes of compounds in order, for example, to reduce the dielectric and/or optical anisotropy of such a dielectric and/or to suppress objectionable smectic phase regions in nematic mixtures. The compounds of the formula I are also suitable for use as intermediate products for the preparation of other substances which can be used as constituents of liquid-crystal phases.

In the pure state, the compounds of the formula I are colourless, and they form liquid-crystal meso-phases within a temperature range which is advantageously situated for electrooptical use. They are very stable to chemicals, heat and light.

The invention relates, therefore, to the compounds of the formula I and to a process for their preparation, characterized in that a compound which otherwise corresponds to the formula I, but contains one or more reducible groups and/or C—C bonds instead of H atoms is treated with a reducing agent or, in order to prepare esters of the formula I, a corresponding carboxylic acid or one of its reactive derivatives is reacted with a corresponding alcohol or one of its reactive derivatives, or, in order to prepare β-keto esters of the formula I, a corresponding cyclohaxanone derivative is subjected to a condensation reaction with a corresponding dialkyl carbonate in the presence of a base, or, in order to prepare ethers of the formula I, a corresponding hydroxy compound is etherified, or, in order to prepare cyclohexanone derivatives of the formula I, a corresponding epoxide is subjected to an acid-catalysed rearrangement.

The invention also relates to the use of the compounds of the formula I as components of liquid-crystal phases. The invention also relates to liquid-crystal phases containing at least one compound of the formula I and to liquid-crystal display elements, in particular electrooptical display elements, containing phases of this type.

The invention also relates to a liquid-crystal phase containing at least two liquid-crystal components, characterized in that it contains at least one transversely polarized 1,4-cyclohexylene compound wherein at least one $CH_2$ group has been replaced by a —CO— group, and/or to a liquid-crystal phase having at least two liquid-crystal components, characterized in that it contains at least one cis-1,3-disubstituted cyclohexane compound.

In the previous and following text, $R^1$, $R^2$, $R^3$, $A^1$, $A^2$, $A^3$, $A^4$, A, $Z^1$ and $Z^2$ have the meaning indicated, unless anything to the contrary is expressly recorded.

Accordingly, the compounds of the formula I embrace, in particular, compounds of the partial formulae Ia and Ib (having two rings)

$R^1$—A—$A^2$—$R^2$     Ia $R^1$—A—$Z^1$—$A^2$—$R^2$     Ib

Ic to Ii (having three rings)

$R^1$—$A^4$—A—$A^2$—$R^2$     Ic $R^1$—A—$A^4$—$A^2$—$R^2$     Id $R^1$—$A^4$—A—$Z^1$—$A^2$—$R^2$     Ie $R^1$—A—$A^4$—$Z^1$—$A^2$—$R^2$     If $R^1$—A—$Z^1$—$A^2$—$A^3$—$R^3$     Ig $R^3$—$A^3$—$Z^2$—A—$Z^1$—$A^2$—$R^2$     Ih $R^1$—A—$Z^1$—$A^2$—$Z^2$—$A^3$—$R^3$     Ii and Ij to It (having four rings)

$R^1$—$A^4$—A—$A^2$—$A^3$—$R^3$     Ij $R^1$—A—$A^4$—$A^2$—$A^3$—$R^3$     Ik $R^3$—$A^3$—$Z^2$—$A^4$—A—$A^2$—$R^2$     Il $R^3$—$A^3$$A^4$—A—$Z^1$$A^2$—$R^2$     Im $R^1$—A—$A^4$—$A^2$—$Z^2$—$A^3$—$R^3$     In $R^1$—A—$A^4$—$Z^1$—$A^2$—$A^3$—$R^3$     Io $R^1$—$A^4$—A—$Z^1$—$A^2$—$A^3$—$R^3$     Ip $R^1$—$A^4$—A—$Z^1$—$A^2$—$Z^2$—$A^3$—$R^3$     Iq $R^1$—A—$A^4$—$Z^1$—$A^2$—$Z^2$—$A^3$—$R^3$     Ir $R^3$—$A^3$—$Z^2$—$A^4$—A—$Z^1$—$A^2$—$R^2$     Is $R^3$—$A^3$—$Z^2$—A—$A^4$—$Z^1$—$A^2$—$R^2$     It

Amongst these, the compounds of the formulae Ia, Ib, Ic, Id, Ie, If, Ig, Ij and Ik are particularly preferred.

The preferred compounds of the formula Ia embrace those of the partial formulae Ia1 to Ia3:

$R^1$—A—Ph—$R^2$     Ia1

$R^1$—A—Cy—$R^2$     Ia2

$R^1$—A—Bi—$R^2$     Ia3

Amongst these, the compounds of the partial formulae Ia1 and Ia2 are particularly preferred.

The preferred compounds of the formula Ib embrace those of the partial formulae Ib1 to Ib3:

$R^1$—A—$Z^1$—Ph—$R^2$     Ib1

$R^1$—A—$Z^1$—Cy—$R^2$     Ib2

$R^1$—A—$Z^1$—Bi—$R^2$     Ib3

Amongst these, the compounds of the partial formulae Ib1 and Ib2, in particular those wherein $Z^1$ is —CO—O—, —O—CO—, —$CH^2$CO—, —CO$CH^2$— or —$CH^2$$CH^2$—, are particularly preferred.

The preferred compounds of the formula Ic embrace those of the partial formulae Ic1 and Ic2:

$R^1$—Cy—A—Cy—$R^2$     Ic1

$R^1$—Cy—A—Ph—$R^2$     Ic2

The preferred compounds of the formula Id embrace those of the partial formulae Id1 to Id4:

$R^1$—A—Cy—Cy—$R^2$     Id1

$R^1$—A—Ph—Ph—$R^2$     Id2

$R^1$—A—Ph—Cy—$R^2$     Id3

$R^1$—A—Cy—Ph—$R^2$     Id4

Amongst these, those of the partial formulae Id1 and Id4 are particularly preferred.

The preferred compounds of the formula Ie embrace those of the partial formulae Ie1 to Ie3:

$R^1$—Cy—A—$Z^2$—Cy—$R^2$     Ie1

$R^1$—Cy—A—$Z^1$—Ph—$R^2$     Ie2

$R^1$—Ph—A—$Z^1$—Cy—$R^2$     Ie3

Amongst these, those of the partial formulae Ie1, in particular those wherein $Z^1$ is —CO—O—, —O—CO— or —$CH_2CH_2$—, are particularly preferred.

The preferred compounds of the formula If embrace those of the partial formulae If1 to If4:

$R^1$—A—Cy—$Z^1$—Cy—$R^2$     If1

$R^1$—A—Ph—$Z^1$—Ph—$R^2$     If2

R¹—A—Ph—Z¹—Cy—R²  If3

R¹—A—Cy—Z¹—Ph—R²  If4

Amongst these, the compounds of the partial formulae If1, If2 and If3, in particular those wherein Z¹ is —CO—O—, —O—CO— or —CH₂CH₂—, especially —CO—O—, are particularly preferred.

The preferred compounds of the formula Ig embrace those of the partial formulae Ig1 to Ig3:

R¹—A—Z¹—Cy—Cy—R³  I1

R¹—A—Z¹—Ph—Cy—R²  Ig2

R¹—A—Z¹—ph—Ph—R²  Ig3

Amongst these, the compounds wherein Z¹ is —O—CO—, —CO—O—, —CH₂CO—, —COCH₂— or —CH₂CH₂— are particuarly preferred. Ph—Ph is preferably 4,4¹-biphenyl or —Pyr—Phe—.

The preferred compounds of the formula Ij embrace those of the partial formulae Ij1 and Ij2:

R¹—Cy—A—Ph—Ph—R³  Ij1

R¹—Cy—A—Ph—Cy—R³  Ij2

The preferred compounds of the formula Ik embrace those of the partial formulae Ik1 and Ik2:

R¹—A—Ph—Ph—Cy—R³  Ik1

R¹—A—Ph—Cy—Cy—R³  Ik2

In the compounds of the above and following formulae, R¹, R² and R³ are preferably alkyl, and also alkoxy or another oxaalkyl group.

Compounds of the above and following formulae which are also preferred are those wherein one of the radicals R¹, R² and R³ is —CO—alkyl, —O—CO—alkyl, —CO—O—alkyl or CN, and the other is alkyl.

In the preferred compounds of the above and following formulae, the alkyl radicals, in which a CH₂ group (alkoxy or oxaalkyl) can also be replaced by an 0 atom, can be linear or branched. Preferably, they are linear and have 2, 3, 4, 5, 6 or 7 C atoms and are, accordingly, preferably ethyl, propyl, butyl, pentyl, hexyl, heptyl, ethoxy, propoxy, butoxy, pentoxy, hexoxy, heptoxy, 2-oxapropyl (=2-methoxymethyl), 2-oxabutyl (=ethoxymethyl) or 3-oxa-butyl (=2-methoxyethyl), 2-, 3-or 4-oxapentyl, 2-, 3-, 4-or 5-oxahexyl, 2-, 3-, 4-, 5-or 6-oxaheptyl, and also methyl, octyl, nonyl, methoxy, octoxy or nonoxy.

A², A³ and A⁴ are preferably Cy or Ph. Z¹ and Z² are preferably single bonds or, as a second preference, —O—CO—, —CO—O—, —CH²CO—, —COCH²— or —CH²CH²— groups. Z⁰ is preferably a single bond.

A is preferably a group selected from the formulae (A) to (F)

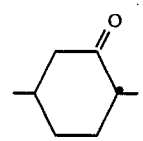
(A)

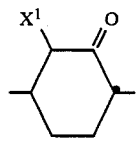
(B)

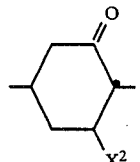
(C)

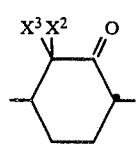
(D)

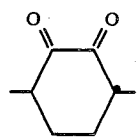
(E)

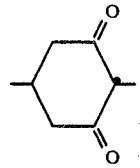
(F)

wherein X¹, X² and X³ independently of one another are each F, Cl, Br, CN, alkyl, alkoxy, oxaalkyl, alkanoyl, alkanoyloxy or alkoxycarbonyl having in each case 1 to 10 C atoms.

A also embraces the mirror images of the formulae (A) to (F).

A is preferably also a group of the formula (G)

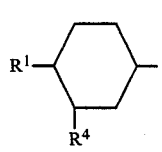
(G)

wherein R⁴ is preferably OH, n-alkyl, n-alkoxy, n-alkanoyloxy, n-alkoxycarbonyl, CN or n-alkanoyl (in each case preferably having 1 to 10 C atoms, in particular 2 to 7 C atoms). R¹ is in this case H. Compounds of the formula I which are particularly preferred are those wherein R¹—A¹—Z¹— is a radical of the formula (H) in the stereochemical configuration indicated:

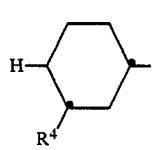
(H)

A is preferably also a group of the formula (J):

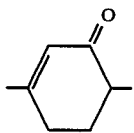

The groups of the formulae (A) to (F) can carry an additional axial substituent Q in the 1-position or 4-position. Q is preferably F, CN or $CH_3$, especially $CH_3$.

Preferred meanings for $X^1$, $X^2$ and $X^3$ are F, Cl, CN, —$CH_3$, —$CH_2CH_3$ and —$OCH_3$. CN and $CH_3$ are particularly preferred for $X^1$, and F, $CH_3$ and CN are particularly preferred for $X^2$ or $X^3$.

The groups (A) and (H) are particularly preferred. Ph is preferably 1,4-phenylene, 2-fluoro-1,4-phenylene, Pyr, Pyn, pyridine-2,5-diyl or pyrazine-2,5-diyl. 1,4-Phenylene and Pyr are particularly preferred.

The compounds of the formula I preferably contain only one ring A.

Compounds of the above and following formulae containing branched wing groups $R^1$, $R^2$ or $R^3$ can occasionally be of importance because of improved solubility in the conventional liquid-crystal base materials, but can be of particular interest as chiral doping substances, if they are optically active. As a rule, branched groups of this type contain not more than one chain branching. Compounds of this type can be used as components of smectic mixtures having ferroelectric properties.

Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Amongst the compounds of the formula I and also Ia to It, preferred compounds are those in which at least one of the radicals contained therein has one of the preferred meanings indicated. Minor groups of compounds which are particularly preferred are those of the formulae I1 to I10

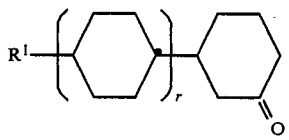

I1

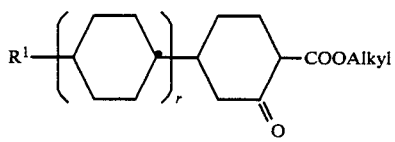

I2

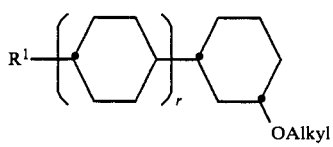

I3

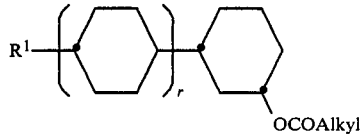

I4

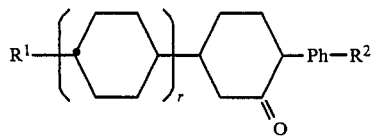

I5

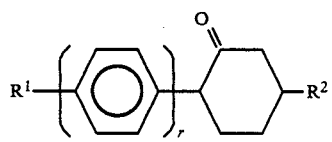

I6

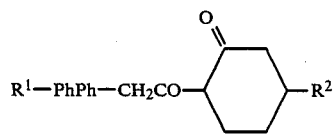

I7

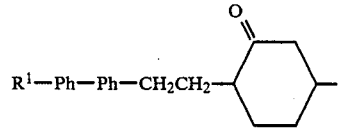

I8

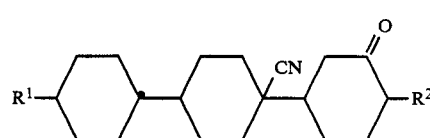

I9

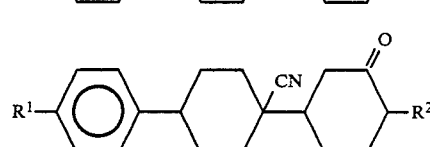

I10

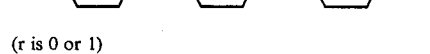

(r is 0 or 1)

Stereoisomers which are preferred in the compounds of the formulae mentioned above are those in which the substituents $R^1$—, $R^1$—$A^4$—, $R^2$—$A^2$—$Z^1$— or $R^2$—$A^2$—$Z^{1-A4}$ in the 1-position and 4-position of the ring A are in the transconfiguration and assume the equatorial position, while the additional substituent Q which is optionally present in the 1-position or 4-position in A occupies an axial position. These are as a rule more stable; in many cases the cis-compounds (or mixtures) can be converted into the transcompounds by treatment with a base, for example with K tert.-butylate, in an inert solvent, such as dimethyl sulfoxide.

The substituents $X^1$, $X^2$ and $X^3$ in the groups of the formulae (B) and (C) can occupy equatorial or axial positions.

Those of the formulae mentioned above which contain one or more Dio, Dit, Pip, pyridine-2,5-diyl and/or Pyr groups include in each case the two possible 2,5-position isomers (Dio, Dit or Pyr) or 1,4-position isomers (Pip), respectively.

The compounds of the formula I are prepared by methods which are in themselves known, such as are described in the literature (for example in the standard works such as Houben-Weyl, Methoden der Organischen Chemie ("Methods of Organic Chemistry"), Georg-Thieme-Verlag, Stuttgart), in particular under reaction conditions which are known and suitable for the reactions mentioned. In this respect it is also possible to make use of variants which are in themselves known but are not mentioned here in detail.

The starting materials can, if desired, also be formed in situ, in such a way that they are not isolated from the reaction mixture, but are immediately reacted further to give the compounds of the formula I.

Thus the compounds of the formula I can be prepared by reducing a compound which otherwise corresponds to the formula I but contains one or more reducible groups and/or C—C bonds instead of H atoms.

Suitable reducible groups are preferably —Ch=CH— groups, and also, for example, free or esterified hydroxyl groups, halogen atoms attached to an aromatic nucleus, or carbonyl groups. Preferred starting materials for the reduction correspond to the formula I, but can contain a —CH=CH— group instead of a —$CH_2CH_2$— group and/or a —CO—group instead of a —$CH_2$— group and/or a free or functionally modified (for example in the form of its p-toluenesulfonate) OH group instead of an H atom.

The reduction can, for example, be effected by catalytic hydrogenation at temperatures between about 0° and about 200° and under pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in an aqueous alcoholic solution or in a heterogeneous$ phase containing water/toluene at temperatures between about 80° and 120°) or of Wolff-Kishner (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I containing alkyl groups and/or —$CH_2CH_2$— bridges.

Reduction by means of complex hydrides is also possible. For example, arylsulfonyloxy groups can be removed reductively by means of $LiAlH_4$, in particular p-toluenesulfonyloxymethyl groups can be reduced to methyl groups, preferably in an inert solvent, such as diethyl ether or THF, at temperatures between about 0° and 100°. Double bonds can be hydrogenated (even in the presence of methanol; thus the corresponding cyclohexane derivatives are formed, for example, from 1-cyanocyclohexene derivatives.

Esters of the formula I can also be obtained by esterifying corresponding carboxylic acids (or reactive derivatives thereof) with alcohols or phenols (or reactive derivatives thereof).

Suitable reactive derivatives of the carboxylic acids mentioned are, in particular, the acid halides, above all the chlorides and bromides, and also the anhydrides, including, for example, mixed anhydrides, azides or esters, in particular alkyl esters having 1-4 C atoms in the alkyl group.

Suitable reactive derivatives of the alcohols or phenols mentioned are, in particular, the corresponding metal alcoholates or phenates, preferably of an alkali metal, such as Na or K.

It is advantageous to carry out the esterification in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, and sulfoxides, such as dimethyl sulfoxide or sulfolane. Water-immiscible solvents can advantageously be used at the same time for removal by azeotropic distillation of the water formed in the esterification. An excess of an organic base, for example pyridine, quinoline or triethylamine, can occasionally also be used as a solvent for the esterification. The esterification can also be carried out in the absence of a solvent, for example merely by heating the components in the presence of sodium acetate. The reaction temperature is usually between $-50°$ and $+250°$, preferably between $-20°$ and $+80°$. At these temperatures the esterification reactions are, as a rule, complete after 15 minutes to 48 hours.

In a particular case, the reaction conditions for the esterification depend largely on the nature of the starting materials used. Thus a free carboxylic acid is as a rule reacted with a free alcohol or phenol in the presence of a strong acid, for example a mineral acid, such as hydrochloric acid or sulfuric acid. A preferred procedure is to react an acid anhydride, or especially an acid chloride, with an alcohol, preferably in a basic medium, in which respect bases of importance are, in particular, alkali metal hydroxides, such as sodium hydroxide or potassium hydroxide, alkali metal carbonates or bicarbonates, such as sodium carbonate, potassium carbonate or potassium bicarbonate, alkali metal acetates, such as sodium acetate or potassium acetate, or alkaline earth metal hydroxides, such as calcium hydroxide, or organic bases, such as triethylamine, pyridine, lutidine, collidine or quinoline. A further preferred embodiment of the esterification consists in first converting the alcohol or the phenol into the sodium or potassium alcoholate or sodium or potassium phenate, respectively, for example by treatment with ethanolic sodium hydroxide or potassium hydroxide solution, isolating this product and suspending it, together with sodium bicarbonate or potassium carbonate, in acetone or diethyl ether, by stirring, and adding to this suspension a solution of the acid chloride or anhydride in diethyl ether, acetone or DMF, preferably at temperatures between about $-25°$ and $+20°$.

Dioxane derivatives or dithiane derivatives of the formula I are preferably prepared by reacting a corresponding aldehyde (or one of its reactive derivatives) with a corresponding 1,3-diol or a corresponding 1,3-dithiol, respectively (or one of their reactive derivatives), preferably in the presence of an inert solvent, such as benzene or toluene, and/or a catalyst, for example a strong acid, such as sulfuric acid or benzenesulfonic or p-toluenesulfonic acid, at temperatures between 20° and about 150°, preferably between 80° and 120°. Suitable reactive derivatives of the starting materials are primarily acetals.

The aldehydes and 1,3-diols or 1,3-dithiols mentioned and their reactive derivatives are in part known; all of them can be prepared without difficulties in accordance with standard processes of organic chemistry from compounds known from the literature. For example, the aldehydes can be obtained by oxidizing corresponding alcohols or by reducing corresponding carboxylic acids or derivatives thereof, the diols can be obtained by reducing corresponding diesters and the dithiols by reacting corresponding dihalides with NaSH.

Nitriles of the formula I can be prepared by dehydrating corresponding acid amides, for example amides in which a CONH2 group takes the place of the radical X. The amides can be obtained, for example, from corresponding esters or acid halides by reaction with ammonia. Examples of suitable dehydrating agents are inorganic acid chlorides, such as SOCl2, PCl3, PCl5, POCl3, SO2Cl2, COCl2 and P2O5, P2S5 and AlCl3 (for example in the form of double compounds with NaCl), aromatic sulfonic acids and sulfonyl halides. This reaction can be carried out in the presence or absence of an inert solvent at temperatures between about 0° and 150°; examples of suitable solvents are bases, such as pyridine or triethylamine, aromatic hydrocarbons, such as benzene, toluene or xylene, or amides, such as DMF.

The abovementioned nitriles of the formula I can also be prepared by reacting corresponding acid halides, preferably the chlorides, with sulfamide, preferably in an inert solvent, such as tetramethylene sulfone, at temperatures between about 80° and 150°, preferably at 120°. The nitriles can be isolated without further treatment after working up in the customary manner.

Ethers of the formula I can be obtained by etherifying corresponding hydroxy compounds, preferably corresponding phenols, it being preferable first to convert the hydroxy compound into a corresponding metal derivative, for example into the corresponding alkali metal alcoholate or alkali metal phenate by treatment with NaH, NaNH2, NaOH, KOH, Na2CO3 or K2CO3. This derivative can then be reacted with the corresponding alkyl halide or sulfonate reacted with the corresponding alkyl halide or sulfonate or dialkyl sulfate, preferably in an inert solvent, such as acetone, 1,2-dimethoxyethane, DMF or dimethylsulfoxide, or an excess of aqueous or aqueous alcoholic NaOH or KOH at temperatures between about 20° and 100°.

Cyclohexanone derivatives of the formula I are also accessible by acid-catalysed rearrangements of the corresponding epoxides by processes known from the literature, for example by treatment with BF3-etherate. The epoxides can be obtained by epoxidizing the corresponding cyclohexene derivatives by standard processes.

Preferred cyclohexane derivatives of the formula I1

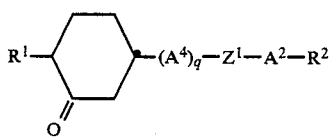

I1 wherein $R^1$ is preferably an alkyl group having 1–10 C atoms, q is 0 or 1 and $A^4$, $Z^1$, $A^2$ and $R^2$ have the meaning indicated in formula I, are also accessible by reacting compounds of the formula I1'

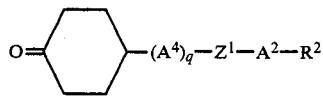

I1' wherein $A^4$, q, $Z^1$, $A^2$ and $R^2$ have the meanings indicated above, with $R^1$-MgX, followed by dehydration, hydroboration and oxidation to give I1 analogously to the method of H. C. Brown and C. P. Garg, J. Am. Chem. Soc. 83, 2951 (1961).

β-Keto esters of the formula I can be obtained, for example, by standard processes by subjecting corresponding cyclohexanone derivatives to a condensation reaction with a dialkyl carbonate in the presence of a base, for example KH.

Nitriles of the formula I can also be prepared by reacting corresponding chlorine or bromine compounds of the formula I with a cyanide, preferably with a metal cyanide, such as NaCN, KCN or Cu2(CN)2, for example in the presence of pyridine in an inert solvent, such as DMF or N-methylpyrrolidone, at temperatures betwen 20° and 200°.

The optically active compounds of the formula I, the asymmetry centre of which can be localized either in the wing groups $R^1$, $R^2$ and $R^3$ or in the groups A and $R^1$—$A^1$—, are obtained by using corresponding optically active starting materials and/or by separating the optical antipodes by means of chromatography, using known methods.

The phases according to the invention preferably contain at least three, in particular at least five, compounds of the formula I. Chirally tilted, smectic liquid-crystal phases, the achiral base mixture of which contains, in addition to compounds of the formula I, at least one other component having a negative dielectric anisotropy or a small amount of a positive dielectric anisotropy, are particularly preferred. These further component(s) of the chiral base mixture can amount to 1 to preferably 10 to 25%, of the base mixture. Suitable further components with small amount of a positive or a negative dielectric anisotropy are compounds of the partial formulae Va to Vp:

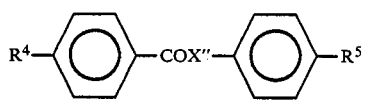

Va

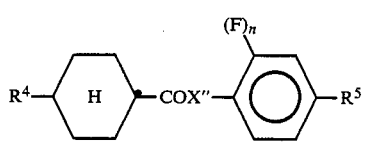

Vb

Vc

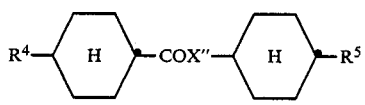

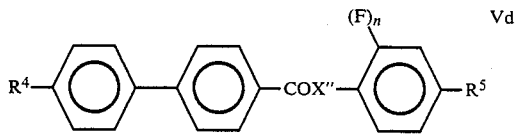

Vd

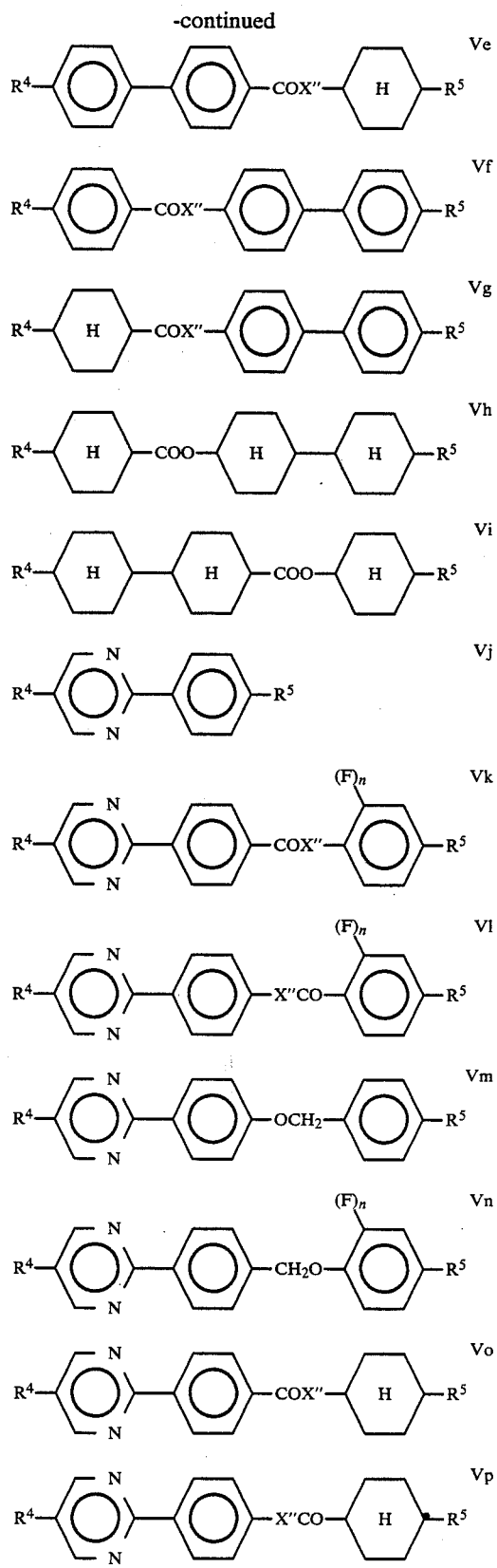

$R^4$ and $R^5$ are in each case preferably straight-chain or singly branched alkyl, alkoxy, alkanoyloxy or alkoxycarbonyl each having 3 to 12 C atoms. $X'''$ is O or S, preferably O. n is 0 or 1.

Those compounds of the partial formulae Va, Vb, vd and vf in which $R^4$ and $R^5$ are each straight-chain alkyl or alkoxy each having 5 to 10 C atoms, are particularly preferred.

The compounds of partial formulae vc, Vh and vi are suitable as additives for lowering the melting point and are normally added to the base mixtures in quantities of not more than 5%, preferably 1 to 3%. In the compounds of the partial formulae Vc, Vh and Vi, $R^4$ and $R^5$ preferably are straight-chain alkyl having 2 to 7, preferably 3 to 5, C atoms. A further class of compounds suitable for lowering the melting point in the phases according to the invention is that of the formula

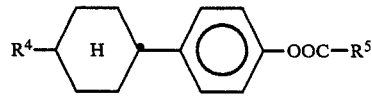

in which $R^4$ and $R^5$ have the preferred meaning given for Vc, Vh and Vi.

Furthermore, other suitable components with a negative dielectric anisotropy are compounds containing the structural element M, N or O.

             M

             N $$-\underset{|}{\overset{Cl}{CH}}-$$             O

Preferred compounds of this type correspond to the formulae VIb and VIc:

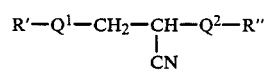      VIb

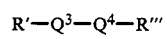      VIc $R'$ and $R''$ each are preferably straight-chain alkyl or alkoxy groups each having 2 to 10 C atoms. $Q^1$ and $Q^2$ are each 1,4-phenylene, trans-1,4-cyclohexylene, 4,4'-biphenylyl, 4-(trans-4-cyclohexyl)-phenyl trans, trans-4,4'-bicyclohexyl, or one of the groups $Q^1$ and $Q^2$ can also be a single bond.

$Q^3$ and $Q^4$ each are 1,4-phenylene, 4,4' biphenylyl or trans-1,4-cyclonexylene. One of the groups $Q^3$ and $Q^4$ can also be 1,4-phenylene in which at least one CH group is replaced by N. $R'''$ is an optically active radical with an asymmetric carbon atom of the structure

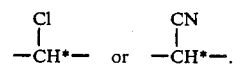

Particularly preferred compounds of the formula VIc are those of the formula VIc':

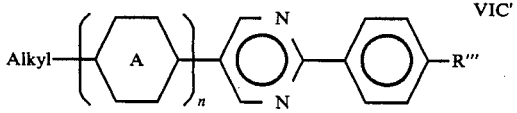

in which A is 1,4-phenylene or trans-1,4-cyclohexylene and n is 0 or 1.

The compounds of the formula I are also suitable as components of nematic liquid-crystal phases, for example for avoiding reverse twist.

These liquid-crystal phases according to the invention consist of 2 to 25, preferably 3 to 15, components, including at least one compound of the formula I. The other constituents are preferably selected from nematic or nematogenic substances, in particular the known substances, belonging to the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenylpyridazines or cyclohexylpyridazines and N-oxides thereof, phenyldioxanes or cyclohexyldioxanes, phenyl-1,3-dithianes or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds which are suitable as constituents of liquid-crystal phases of this type can be characterized by the formula I'

$$R'\text{—}L\text{—}G\text{—}E\text{—}R'' \qquad I'$$

wherein L and E are each a carbocyclic or heterocyclic ring system belonging to the group formed from 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydronaphthalene and tetrahydronaphthalene, quinazoline and tetrahydroquinazoline,

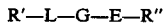

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —C—N, and R' and R" are alkyl, alkoxy, alkanoyloxy, alkoxycarbonyl or alkoxycarbonyloxy having up to 18, preferably up to 8, carbon atoms, or one of these radicals is also CN, NC, NO$_2$, CF$_3$, F, Cl or Br.

In most of these compounds R' and R" are different from one another, one of these radicals being in most cases an alkyl or alkoxy group. Other variants of the substituents envisaged are, however, also customary. Many of such substances or mixtures thereof are commercially available. All these substances can be obtained by methods known from the literature.

The phases according to the invention contain about 0.1 to 99%, preferably 10 to 95%, of one or more compounds of the formula I. Liquid-crystal phases according to the invention containing 0.1–40%, preferably 0.5–30%, of one or more compounds of the formula I are also preferred.

The phases according to the invention are prepared in a manner which is in itself customary. As a rule, the components are dissolved in one another, preferably at an elevated temperature.

By means of suitable additives it is possible to modify the liquid-crystal phases according to the invention in such a way that they can be used in all the types of liquid-crystal display elements which have hitherto been disclosed.

Additives of this type are known to those skilled in the art and are described in detail in the literature. For example, it is possible to add conducting salts, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst. volume 24, pages 249–258 (1973)) in order to improve the conductivity, and pleochroic dyestuffs in order to prepare coloured guest-host systems or substances for varying the dielectric anisotropy, the viscosity and/or the orientation of the nematic phases. Substances of this type are described, for example, in German Offenlegungsschriften 2,209,127, 2,240,864, 2,321,632, 2,338,281, 2,450,088, 2,637,430, 2,853,728 and 2,902,177.

The examples which follow are intended to illustrate the invention without limiting it. M.p.=melting point and c.p. =clear point. In the preceding and following text percentages are percentages by weight; all temperatures are quoted in degrees Celsius. "Customary working up" means the following: water is added, the mixture is extracted with methylene chloride, the phases are separated, the organic phase is dried and evaporated and the product is purified by crystallization and/or chromatography.

EXAMPLE 1

A solution of 6.5 g of 3-[trans-4-(trans-4-n-propylcyclohexyl)-cyclohexyl]-cyclohex-2-enone [m.p. 96.5°; obtainable by reacting trans-4-(trans-4-n-propycyclohexyl)-acetylcyclohexane with LDA/ether at −85°, adding 1-(trimethylsilyl)-vinyl methyl ketone at −95°, allowing the mixture to warm up to room temperature, adding methanolic KOH and working up in the customary manner (silica gel; 5:3.5:1.5 petroleum ether:methylene chloride:ether)] in 210 ml of ethanol is added to a suspension of 1.7 g of 5% Pd/CaCO$_3$ in 75 ml of ethanol, and the mixture is stirred under hydrogen for 2 hours. Removing the catalyst and working up in the customary manner gives 3-[trans-4-(trans-4-n-propylcyclohexyl)-cyclohexyl]-cyclohexanone, m.p. 1.5°, c.p. 158.2°

The following are prepared analogously:
3-[trans-4-(trans-4-ethylcyclohexyl)-cyclohexyl]-cyclohexanone
3-[trans-4-(trans-4-butylcyclohexyl)-cyclohexyl]-cyclohexanone
3-[trans-4-(trans-4-pentylcyclohexyl)-cyclohexyl]-cyclohexanone
3-[trans-4-(trans-4-hexylcyclohexyl)-cyclohexyl]-cyclohexanone
3-[trans-4-(trans-4-heptylcyclohexyl)-cyclohexyl]-cyclohexanone
3-(trans-4-ethylcyclohexyl)-cyclohexanone
3-(trans-4-propylcyclohexyl)-cyclohexanone
3-(trans-4-butylcyclohexyl)-cyclohexanone 3-(trans-4-pentylcyclohexyl)-cyclohexanone
3-(trans-4-heptylcyclohexyl)-cyclohexanone
3-(trans-4-ethylcyclohexyl)-6-propylcyclohexanone
3-(trans-4-propylcyclohexyl)-6-propylcyclohexanone
3-(trans-4-butylcyclohexyl)-6-propylcyclohexanone
3-(trans-4-pentylcyclohexyl)-6-propylcyclohexanone
3-(trans-4-heptylcyclohexyl)-6-propylcyclohexanone
3-(trans-4-ethylcyclohexyl)-6-butylcyclohexanone
3-(trans-4-propylcyclohexyl)-6-butylcyclohexanone
3-(trans-4-butylcyclohexyl)-6-butylcyclohexanone
3-(trans-4-pentylcyclohexyl)-6-butylcyclohexanone
3-(trans-4-heptylcyclohexyl)-6-butylcyclohexanone
3-(trans-4-ethylcyclohexyl)-6-pentylcyclohexanone
3-(trans-4-propylcyclohexyl)-6-pentylcyclohexanone
3-(trans-4-butylcyclohexyl)-6-pentylcyclohexanone
3-(trans-4-pentylcyclohexyl)-6-pentylcyclohexanone
3-(trans-4-heptylcyclohexyl)-6-pentylcyclohexanone

EXAMPLE 2

7.5 mmol of KH and 40 ml of dimethyl carbonate are added to a solution of 2.0 g of 3-[trans-4-(trans-4-n-propylcyclohexyl)-cyclohexyl]-cyclohexanone (Example 1) in 40 ml of THF, and the mixture is boiled for 2 hours. Customary working up (silica gel; 6.5:3:0.5 petroleum ether: methylene chloride:ether) gives methyl 4-[trans-4-(trans-4-n-propylcyclohexyl)-cyclohexyl]-2-oxocyclohexanecarboxylate, which is predominantly in the enol form, m.p. 154°, c.p. 192°.

The following are prepared analogously:
ethyl 4-[trans-4-(trans-4-propylcyclohexyl)-cyclohexyl]-2-oxocyclohexanecarboxylate
propyl 4-[trans-4-(trans-4-propylcyclohexyl)-cyclohexyl]-2-oxocyclohexanecarboxylate
butyl 4-[trans-4-(trans-4-propylcyclohexyl)-cyclohexyl]-2-oxocyclohexanecarboxylate
pentyl 4-[trans-4-(trans-4-propylcyclohexyl)-cyclohexyl]-2-oxocyclohexanecarboxylate
methyl 4-[trans-4-(trans-4-butylcyclohexyl)-cyclohexyl]-2-oxocyclohexanecarboxylate
ethyl 4-[trans-4-(trans-4-butylcyclohexyl)-cyclohexyl]-2-oxocyclohexanecarboxylate
propyl 4-[trans-4-(trans-4-butylcyclohexyl)-cyclohexyl]-2-oxocyclohexanecarboxylate
butyl 4-[trans-4-(trans-4-butylcyclohexyl)-cyclohexyl]-2-oxocyclohexanecarboxylate
pentyl 4-[trans-4-(trans-4-butylcyclohexyl)-cyclohexyl]-2-oxocyclohexanecarboxylate
methyl 4-[trans-4-(trans-4-pentylcyclohexyl)-cyclohexyl]-2-oxocyclohexanecarboxylate
ethyl 4-[trans-4-(trans-4-pentylcyclohexyl)-cyclohexyl]-2-oxocyclohexanecarboxylate
propyl 4-[trans-4-(trans-4-pentylcyclohexyl)-cyclohexyl]-2-oxocyclohexanecarboxylate
butyl 4-[trans-4-(trans-4-pentylcyclohexyl)-cyclohexyl]-2-oxocyclohexanecarboxylate
pentyl 4-[trans-4-(trans-4-pentylcyclohexyl)-cyclohexyl]-2-oxocyclohexanecarboxylate
methyl 4-(trans-4-propylcyclohexyl)-2-oxocyclohexanecarboxylate
ethyl 4-(trans-4-propylcyclohexyl)-2-oxocyclohexanecarboxylate
propyl 4-(trans-4-propylcyclohexyl)-2-oxocyclohexanecarboxylate
butyl 4-(trans-4-propylcyclohexyl)-2-oxocyclohexanecarboxylate
pentyl 4-(trans-4-propylcyclohexyl)-2-oxocyclohexanecarboxylate
methyl 4-(trans-4-butylcyclohexyl)-2-oxocyclohexanecarboxylate
ethyl 4-(trans-4-butylcyclohexyl)-2-oxocyclohexanecarboxylate
propyl 4-(trans-4-butylcyclohexyl)-2-oxocyclohexanecarboxylate
butyl 4-(trans-4-butylcyclohexyl)-2-oxocyclohexanecarboxylate
pentyl 4-(trans-4-butylcyclohexyl)-2-oxocyclohexanecarboxylate
methyl 4-(trans-4-pentylcyclohexyl)-2-oxocyclohexanecarboxylate
ethyl 4-(trans-4-pentylcyclohexyl)-2-oxocyclohexanecarboxylate
propyl 4-(trans-4-pentylcyclohexyl)-2-oxocyclohexanecarboxylate
butyl 4-(trans-4-pentylcyclohexyl)-2-oxocyclohexanecarboxylate
pentyl 4-(trans-4-pentylcyclohexyl)-2-oxocyclohexanecarboxylate

EXAMPLE 3

A solution of 250 mg of 3-[trans-4-(trans-4-n-propylcyclohexyl)-cyclohexyl]-cyclohex-2-enone (synthesis described in Example 1) in 9 ml of THF is added dropwise to a solution of 55 mg of lithium in 150 ml of NH$_3$, the mixture is stirred for 2 hours, 2 ml of methanol are added, a further 250 mg of lithium are added, the mixture is stirred for 1 hour and neutralized with ammonium chloride, 50 ml of methylene chloride are added, the NH$_3$ is removed and the residue is worked up in the customary manner (6.5:3:0.6 petroleum ether:methylene chloride:ether). r-1-Hydroxy-cis-3-[trans-4-(trans-4-n-propylcyclohexyl)cyclohexyl-]-cyclohexane, m.p. 217°, is obtained.

The following are prepared analogously:
r-1-hydroxy-cis-3-[trans-4-(trans-4-ethylcyclohexyl)cyclohexyl]-cyclohexane
r-1-hydroxy-cis-3-[trans-4-(trans-4-butylcyclohexyl)cyclohexyl]-cyclohexane
r-1-hydroxy-cis-3-[trans-4-(trans-4-pentylcyclohexyl)cyclohexyl]-cyclohexane
r-1-hydroxy-cis-3-[trans-4-(trans-4-heptylcyclohexyl)cyclohexyl]-cyclohexane
r-1-hydroxy-cis-3-(trans-4-ethylcyclohexyl)-cyclohexane
r-1-hydroxy-cis-3-(trans-4-propylcyclohexyl)-cyclohexane
r-1-hydroxy-cis-3-(trans-4-butylcyclohexyl)-cyclohexane
r-1-hydroxy-cis-3-(trans-4-pentylcyclohexyl)-cyclohexane
r-1-hydroxy-cis-3-(trans-4-heptylcyclohexyl)-cyclohexane

EXAMPLE 4

13 mg of butyryl chloride are added to a solution of 18 mg of r-1-hydroxy-cis-3-[trans-4-(trans-4-n-propylcyclohexyl)-cyclohexyl]-cyclohexane (Example 3) in 1.5 ml of pyridine, and the mixture is stirred for 15 hours and worked up in the customary manner to give r-1-butyryloxy-cis-3-[trans-4-(trans-4-n-propylcyclohexyl)-cyclohexyl]-cyclohexane, m.p. 67.5°, c.p. 91.9°.

The following are prepared analogously:
r-1-acetoxy-cis-3-[trans-4-(trans-4-propylcyclohexyl)cyclohexyl]-cyclohexane
r-1-propionyloxy-cis-3-[trans-4-(trans-4-propylcyclohexyl)cyclohexyl]-cyclohexane r-1-pentanoyloxy-cis-3-[trans-4-(trans-4-propylcyclohexyl)cyclohexyl]-cyclohexane
r-1-acetoxy-cis-3-[trans-4-(trans-4-butylcyclohexyl)cyclohexyl]-cyclohexane
r-1-propionyloxy-cis-3-[trans-4-(trans-4-butylcyclohexyl)cyclohexyl]-cyclohexane
r-1-butyryloxy-cis-3-[trans-4-(trans-4-butylcyclohexyl)cyclohexyl]-cyclohexane
r-1-pentanoyloxy-cis-3-[trans-4-(trans-4-butylcyclohexyl)cyclohexyl]-cyclohexane
r-1-acetoxy-cis-3-[trans-4-(trans-4-pentylcyclohexyl)cyclohexyl]-cyclohexane
r-1-propionyloxy-cis-3-[trans-4-(trans-4-pentylcyclohexyl)cyclohexyl]-cyclohexane
r-1-butyryloxy-cis-3-[trans-4-(trans-4-pentylcyclohexyl)cyclohexyl]-cyclohexane
r-1-pentanoyloxy-cis-3-[trans-4-(trans-4-pentylcyclohexyl)cyclohexyl]-cyclohexane
r-1-acetoxy-cis-3-(trans-4-propylcyclohexyl)-cyclohexane
r-1-propionyloxy-cis-3-(trans-4-propylcyclohexyl)-cyclohexane
r-1-butyryloxy-cis-3-(trans-4-propylcyclohexyl)-cyclohexane
r-1-pentanoyloxy-cis-3-(trans-4-propylcyclohexyl)-cyclohexane
r-1-acetoxy-cis-3-(trans-4-butylcyclohexyl)-cyclohexane
r-1-propionyloxy-cis-3-(trans-4-butylcyclohexyl)-cyclorhexane
r-1-butyryloxy-cis-3-(trans-4-butylcyclohexyl)-cyclohexane
r-1-pentanoyloxy-cis-3-(trans-4-butylcyclohexyl)-cyclohexane
r-1-acetoxy-cis-3-(trans-4-pentylcyclohexyl)-cyclohexane
r-1-propionyloxy-cis-3-(trans-4-pentylcyclohexyl)-cyclohexane
r-1-butyryloxy-cis-3-(trans-4-pentylcyclohexyl)-cyclohexane
r-1-pentanoyloxy-cis-3-(trans-4-pentylcyclohexyl)-cyclohexane

EXAMPLE 5

0.5 g of a 35% KH dispersion is added to a solution of 1.1 g of r-1-hydroxy-cis-3-[trans-4-(trans-4-n-propylcyclohexyl)-cyclohexyl]-cyclohexane (Example 3) in 200 ml of THF, and the mixture is stirred for 2 hours under reflux. 0.6 g of n-iodobutane is then added, the mixture is stirred for two hours at room temperature, excess potassium hydride is destroyed with water, and the mixture is worked up in the customary manner. This gives
r-1-n-butoxy-cis-3-[trans-4-(trans-4-n-propylcyclohexyl)cyclohexyl]-cyclohexane.

The following are prepared analogously:
r-1-methoxy-cis-3-[trans-4-(trans-4-propylcyclohexyl)cyclohexyl]-cyclohexane
r-1-ethoxy-cis-3-[trans-4-(trans-4-propylcyclohexyl)cyclohexyl]-cyclohexane
r-1-propoxy-cis-3-[trans-4-(trans-4-propylcyclohexyl)cyclohexyl]-cyclohexane
r-1-pentoxy-cis-3-[trans-4-(trans-4-propylcyclohexyl)cyclohexyl]-cyclohexane
r-1-methoxy-cis-3-[trans-4-(trans-4-butylcyclohexyl)cyclohexyl]-cyclohexane
r-1-ethoxy-cis-3-[trans-4-(trans-4-butylcyclohexyl)cyclohexyl]-cyclohexane
r-1-propoxy-cis-3-[trans-4-(trans-4-butylcyclohexyl)cyclohexyl]-cyclohexane
r-1-butoxy-cis-3-[trans-4-(trans-4-butylcyclohexyl)cyclohexyl]-cyclohexane
r-1-pentoxy-cis-3-[trans-4-(trans-4-butylcyclohexyl)cyclohexyl]-cyclohexane
r-1-methoxy-cis-3-[trans-4-(trans-4-pentylcyclohexyl)cyclohexyl]-cyclohexane
r-1-ethoxy-cis-3-[trans-4-(trans-4-pentylcyclohexyl)cyclohexyl]-cyclohexane
r-1-propoxy-cis-3-[trans-4-(trans-4-pentylcyclohexyl)cyclohexyl]-cyclohexane
r-1-butoxy-cis-3-[trans-4-(trans-4-pentylcyclohexyl)cyclohexyl]-cyclohexane
r-1-pentoxy-cis-3-[trans-4-(trans-4-pentylcyclohexyl)cyclohexyl]-cyclohexane
r-1-methoxy-cis-3-(trans-4-propylcyclohexyl)-cyclohexane
r-1-ethoxy-cis-3-(trans-4-propylcyclohexyl)-cyclohexane
r-1-propoxy-cis-3-(trans-4-propylcyclohexyl)-cyclohexane
r-1-butoxy-cis-3-(trans-4-propylcyclohexyl)-cyclohexane
r-1-pentoxy-cis-3-(trans-4-propylcyclohexyl)-cyclohexane
r-1-methoxy-cis-3-(trans-4-butylcyclohexyl)-cyclohexane
r-1-ethoxy-cis-3-(trans-4-butylcyclohexyl)-cyclohexane
r-1-propoxy-cis-3-(trans-4-butylcyclohexyl)-cyclohexane
r-1-butoxy-cis-3-(trans-4-butylcyclohexyl)-cyclohexane
r-1-pentoxy-cis-3-(trans-4-butylcyclohexyl)-cyclohexane
r-1-methoxy-cis-3-(trans-4-pentylcyclohexyl)-cyclohexane
r-1-ethoxy-cis-3-(trans-4-pentylcyclohexyl)-cyclohexane
r-1-propoxy-cis-3-(trans-4-pentylcyclohexyl)-cyclohexane
r-1-butoxy-cis-3-(trans-4-pentylcyclohexyl)-cyclohexane
r-1-pentoxy-cis-3-(trans-4-pentylcyclohexyl)-cyclohexane

EXAMPLE 6

15 g of m-chloroperbenzoic acid are added at 0° to a solution of 20 g of p-(4-n-propylcyclohex-1-en-1-yl)-n-pentylbenzene (German Offenlegungsschrift 3,006,666) in 100 ml of ether, and the mixture is stirred for 16 hours. The reaction mixture is extracted several times with 10% sodium hydroxide solution, and the organic phase is dried with sodium sulfate. 40 ml of BF$_3$/ether complex (50% of BF$_3$) are added to the resulting solution of epoxide, and the mixture is stirred for 5 minutes and is then poured onto ice. Working up in the customary manner gives trans-2-(p-n-pentylphenyl)-5-n-propylcyclohexanone. b.p. (0.1 mm Hg) 140°, c.p. −10°.

The following are prepared analogously:
trans-2-(p-pentylphenyl)-5-methylcyclohexanone
trans-2-(p-pentylphenyl)-5-ethylcyclohexanone
trans-2-(p-pentylphenyl)-5-butylcyclohexanone
trans-2-(p-pentylphenyl)-5-pentylcyclohexanone
trans-2-(p-butylphenyl)-5-methylcyclohexanone
trans-2-(p-butylphenyl)-5-ethylcyclohexanone
trans-2-(p-butylphenyl)-5-propylcyclohexanone
trans-2-(p-butylphenyl)-5-butylcyclohexanone trans-2-(p-butylphenyl)-5-pentylcyclohexanone
trans-2-(p-propylphenyl)-5-methylcyclohexanone
trans-2-(p-propylphenyl)-5-ethylcyclohexanone
trans-2-(p-propylphenyl)-5-propylcyclohexanone
trans-2-(p-propylphenyl)-5-butylcyclohexanone,
trans-2-(p-propylphenyl)-5-pentylcyclohexanone, m.p. 38° c.p. 17° (monotropic)
trans-2-(p-ethylphenyl)-5-methylcyclohexanone
trans-2-(p-ethylphenyl)-5-ethylcyclohexanone
trans-2-(p-ethylphenyl)-5-propylcyclohexanone
trans-2-(p-ethylphenyl)-5-butylcyclohexanone
trans-2-(p-ethylphenyl)-5-pentylcyclohexanone
trans-2-(p-methoxyphenyl)-5-methylcyclohexanone
trans-2-(p-methoxyphenyl)-5-ethylcyclohexanone
trans-2-(p-methoxyphenyl)-5-propylcyclohexanone
trans-2-(p-methoxyphenyl)-5-butylcyclohexanone
trans-2-(p-methoxyphenyl)-5-pentylcyclohexanone
trans-2-(p-ethoxyphenyl)-5-methycyclohexanone
trans-2-(p-ethoxyphenyl)-5-ethylcyclohexanone
trans-2-(p-ethoxyphenyl)-5-propylcyclohexanone
trans-2-(p-ethoxyphenyl)-5-butylcyclohexanone
trans-2-(p-ethoxyphenyl)-5-pentylcyclohexanone
trans-2-(p-propoxyphenyl)-5-methylcyclohexanone
trans-2-(p-propoxyphenyl)-5-ethylcyclohexanone
trans-2-(p-propoxyphenyl)-5-propylcyclohexanone
trans-2-(p-propoxyphenyl)-5-butylcyclohexanone
trans-2-(p-propoxyphenyl)-5-pentylcyclohexanone
trans-2-(p-butoxyphenyl)-5-methylcyclohexanone
trans-2-(p-butoxyphenyl)-5-ethylcyclohexanone
trans-2-(p-butoxyphenyl)-5-propylcyclohexanone
trans-2-(p-butoxyphenyl)-5-butylcyclohexanone
trans-2-(p-butoxyphenyl)-5-pentylcyclohexanone
trans-2-(p-pentoxyphenyl)-5-methylcyclohexanone
trans-2-(p-pentoxyphenyl)-5-ethylcyclohexanone
trans-2-(p-pentoxyphenyl)-5-propylcyclohexanone
trans-2-(p-pentoxyphenyl)-5-butylcyclohexanone
trans-2-(p-pentoxyphenyl)-5-pentylcyclohexanone
trans-2-(p-hexoxyphenyl)-5-methylcyclohexanone
trans-2-(p-hexoxyphenyl)-5-ethylcyclohexanone
trans-2-(p-hexoxyphenyl)-5-propylcyclohexanone
trans-2-(p-hexoxyphenyl)-5-butylcyclohexanone
trans-2-(p-hexoxyphenyl)-5-pentylcyclohexanone
trans-2-(p-heptoxyphenyl)-5-methylcyclohexanone
trans-2-(p-heptoxyphenyl)-5-ethylcyclohexanone
trans-2-(p-heptoxyphenyl)-5-propylcyclohexanone
trans-2-(p-heptoxyphenyl)-5-butylcyclohexanone
trans-2-(p-heptoxyphenyl)-5-pentylcyclohexanone
trans-2-(p-octoxyphenyl)-5-methylcyclohexanone
trans-2-(p-octoxyphenyl)-5-ethylcyclohexanone
trans-2-(p-octoxyphenyl)-5-propylcyclohexanone
trans-2-(p-octoxyphenyl)-5-butylcyclohexanone
trans-2-(p-octoxyphenyl)-5-pentylcyclohexanone
trans-2-(p-nonoxyphenyl)-5-methylcyclohexanone
trans-2-(p-nonoxyphenyl)-5-ethylcyclohexanone
trans-2-(p-nonoxyphenyl)-5-propylcyclohexanone
trans-2-(p-nonoxyphenyl)-5-butylcyclohexanone
trans-2-(p-nonoxyphenyl)-5-pentylcyclohexanone
trans-2-(p-cyanophenyl)-5-methylcyclohexanone
trans-2-(p-cyanophenyl)-5-ethylcyclohexanone
trans-2-(p-cyanophenyl)-5-propylcyclohexanone
trans-2-(p-cyanophenyl)-5-butylcyclohexanone
trans-2-(p-cyanophenyl)-5-pentylcyclohexanone
trans-2-(4-pentylbiphenyl-4'-yl)-5-methylcyclohexanone
trans-2-(4-pentylbiphenyl-4'-yl)-5-ethylcyclohexanone
trans-2-(4-pentylbiphenyl-4'-yl)-5-propylcyclohexanone
trans-2-(4-pentylbiphenyl-4'-yl)-5-butylcyclohexanone
trans-2-(4-pentylbiphenyl-4'-yl)-5-pentylcyclohexanone
trans-2-(4-heptylbiphenyl-4'-yl)-5-methylcyclohexanone
trans-2-(4-heptylbiphenyl-4'-yl)-5-ethylcyclohexanone
trans-2-(4-heptylbiphenyl-4'-yl)-5-propylcyclohexanone
trans-2-(4-heptylbiphenyl-4'-yl)-5-butylcyclohexanone
trans-2-(4-heptylbiphenyl-4'-yl)-5-pentylcyclohexanone
trans-2-(4-methoxybiphenyl-4'-yl)-5-methylcyclohexanone
trans-2-(4-methoxybiphenyl-4'-yl)-5-ethylcyclohexanone
trans-2-(4-methoxybiphenyl-4'-yl)-5-propylcyclohexanone
trans-2-(4-methoxybiphenyl-4'-yl)-5-butylcyclohexanone
trans-2-(4-methoxybiphenyl-4'-yl)-5-pentylcyclohexanone
trans-2-(4-ethoxybiphenyl-4'-yl)-5-methylcyclohexanone
trans-2-(4-ethoxybiphenyl-4'-yl)-5-ethylcyclohexanone
trans-2-(4-ethoxybiphenyl-4'-yl)-5-propylcyclohexanone
trans-2-(4-ethoxybiphenyl-4'-yl)-5-butylcyclohexanone
trans-2-(4-ethoxybiphenyl-4'-yl)-5-pentylcyclohexanone
trans-2-(4-propoxybiphenyl-4'-yl)-5-methylcyclohexanone
trans-2-(4-propoxybiphenyl-4'-yl)-5-ethylcyclohexanone
trans-2-(4-propoxybiphenyl-4'-yl)-5-propylcyclohexanone
trans-2-(4-propoxybiphenyl-4'-yl)-5-butylcyclohexanone
trans-2-(4-propoxybiphenyl-4'-yl)-5-pentylcyclohexanone
trans-2-(4-butoxybiphenyl-4'-yl)-5-methylcyclohexanone
trans-2-(4-butoxybiphenyl-4'-yl)-5-ethylcyclohexanone
trans-2-(4-butoxybiphenyl-4'-yl)-5-propylcyclohexanone
trans-2-(4-butoxybiphenyl-4'-yl)-5-butylcyclohexanone
trans-2-(4-butoxybiphenyl-4'-yl)-5-pentylcyclohexanone
trans-2-(4-pentoxybiphenyl-4'-yl)-5-methylcyclohexanone
trans-2-(4-pentoxybiphenyl-4'-yl)-5-ethylcyclohexanone
trans-2-(4-pentoxybiphenyl-4'-yl)-5-propylcyclohexanone
trans-2-(4-pentoxybiphenyl-4'-yl)-5-butylcyclohexanone
trans-2-(4-pentoxybiphenyl-4'-yl)-5-pentylcyclohexanone
trans-2-(4-hexoxybiphenyl-4'-yl)-5-methylcyclohexanone
trans-2-(4-hexoxybiphenyl-4'-yl)-5-ethylcyclohexanone
trans-2-(4-hexoxybiphenyl-4'-yl)-5-propylcyclohexanone
trans-2-(4-hexoxybiphenyl-4'-yl)-5-butylcyclohexanone
trans-2-(4-hexoxybiphenyl-4'-yl)-5-pentylcyclohexanone
trans-2-(4-heptoxybiphenyl-4'-yl)-5-methylcyclohexanone
trans-2-(4-heptoxybiphenyl-4'-yl)-5-ethylcyclohexanone
trans-2-(4-heptoxybiphenyl-4'-yl)-5-propylcyclohexanone trans-2-(4-heptoxybiphenyl-4'-yl)-5-butylcyclohexanone
trans-2-(4-heptoxybiphenyl-4'-yl)-5-pentylcyclohexanone
trans-2-(4-octoxybiphenyl-4'-yl)-5-methylcyclohexanone
trans-2-(4-octoxybiphenyl-4'-yl)-5-ethylcyclohexanone
trans-2-(4-octoxybiphenyl-4'-yl)-5-propylcyclohexanone
trans-2-(4-octoxybiphenyl-4'-yl)-5-butylcyclohexanone
trans-2-(4-octoxybiphenyl-4'-yl)-5-pentylcyclohexanone
trans-2-(4-nonoxybiphenyl-4'-yl)-5-methylcyclohexanone
trans-2-(4-nonoxybiphenyl-4'-yl)-5-ethylcyclohexanone
trans-2-(4-nonoxybiphenyl-4'-yl)-5-propylcyclohexanone
trans-2-(4-nonoxybiphenyl-4'-yl)-5-butylcyclohexanone
trans-2-(4-nonoxybiphenyl-4'-yl)-5-pentylcyclohexanone

EXAMPLE 7

A solution in 180 ml of ethanol of 7.2 g of 1-n-pentyl-5-[trans-4-(trans-4-n-propylcyclohexyl)-cyclohexyl]-cyclohex-1-ene [obtainable by reacting 3-[trans-4-(trans-4-n-propylcyclohexyl)-cyclohexyl]-cyclohexanone (Example 1) with n-pentylmagnesium bromide with subsequent dehydraation] is hydrogenated at room temperature and normal pressure in the presence of 1.2 g of 5% palladium/active charcoal. Working up in the customary manner gives r-1-n-pentyl-cis-3-[trans-4-(trans-4-n-propylcyclohexyl)cyclohexyl]-cyclohexane.

The following are prepared analogously:
r-1-pentyl-cis-3-[trans-4-(trans-4-ethylcyclohexyl)cyclohexyl]-cyclohexane
r-1-pentyl-cis-3-[trans-4-(trans-4-butylcyclohexyl)cyclohexyl]-cyclohexane
r-1-pentyl-cis-3-[trans-4-(trans-4-pentylcyclohexyl)cyclohexyl]-cyclohexane
r-1-heptyl-cis-3[trans-4-(trans-4-ethylcyclohexyl)cyclohexyl]-cyclohexane
r-1-heptyl-cis-3[trans-4-(trans-4-propylcyclohexyl)cyclohexyl]-cyclohexane
r-1-heptyl-cis-3[trans-4-(trans-4-butylcyclohexyl)cyclohexyl]-cyclohexane
r-1-heptyl-cis-3[trans-4-(trans-4-pentylcyclohexyl)cyclohexyl]-cyclohexane
r-1-heptyl-cis-3[trans-4-(trans-4-heptylcyclohexyl) cyclohexyl]-cyclohexane
r-1-butyl-cis-3[trans-4-(trans-4-ethylcyclohexyl)cyclohexyl]-cyclohexane
r-1-butyl-cis-3[trans-4-(trans-4-propylcyclohexyl)cyclohexyl]-cyclohexane
r-1-butyl-cis-3[trans-4-(trans-4-butylcyclohexyl)cyclohexyl]-cyclohexane
r-1-butyl-cis-3[trans-4-(trans-4-pentylcyclohexyl)cyclohexyl]-cyclohexane
r-1-butyl-cis-3[trans-4-(trans-4-heptylcyclohexyl)cyclohexyl]-cyclohexane
r-1-propyl-cis-3[trans-4-(trans-4-ethylcyclohexyl)cyclohexyl]-cyclohexane
r-1-propyl-cis-3[trans-4-(trans-4-propylcyclohexyl)cyclohexyl]-cyclohexane
r-1-propyl-cis-3[trans-4-(trans-4-butylcyclohexyl)cyclohexyl]-cyclohexane
r-1-propyl-cis-3[trans-4-(trans-4-pentylcyclohexyl)cyclohexyl]-cyclohexane
r-1-propyl-cis-3[trans-4-(trans-4-heptylcyclohexyl)cyclohexyl]-cyclohexane
r-1-ethyl-cis-3[trans-4-(trans-4-ethylcyclohexyl)cyclohexyl]-cyclohexane
r-1-ethyl-cis-3[trans-4-(trans-4-propylcyclohexyl)cyclohexyl]-cyclohexane
r-1-ethyl-cis-3[trans-4-(trans-4-butylcyclohexyl)cyclohexyl]-cyclohexane
r-1-ethyl-cis-3[trans-4-(trans-4-pentylcyclohexyl)cyclohexyl]-cyclohexane
r-1-ethyl-cis-3[trans-4-(trans-4-heptylcyclohexyl)cyclohexyl]-cyclohexane
r-1-heptyl-cis-3-(trans-4-ethylcyclohexyl)-cyclohexane
r-1-heptyl-cis-3-(trans-4-propylcyclohexyl)-cyclohexane
r-1-heptyl-cis-3-(trans-4-butylcyclohexyl)-cyclohexane
r-1-heptyl-cis-3-(trans-4-pentylcyclohexyl)-cyclohexane
r-1-heptyl-cis-3-(trans-4-heptylcyclohexyl)-cyclohexane
r-1-pentyl-cis-3-(trans-4-ethylcyclohexyl)-cyclohexane
r-1-pentyl-cis-3-(trans-4-propylcyclohexyl)-cyclohexane
r-1-pentyl-cis-3-(trans-4-butylcyclohexyl)-cyclohexane
r-1-pentyl-cis-3-(trans-4-pentylcyclohexyl)-cyclohexane
r-1-pentyl-cis-3-(trans-4-heptylcyclohexyl)-cyclohexane
r-1-butyl-cis-3-(trans-4-ethylcyclohexyl)-cyclohexane
r-1-butyl-cis-3-(trans-4-propylcyclohexyl)-cyclohexane
r-1-butyl-cis-3-(trans-4-butylcyclohexyl)-cyclohexane
r-1-butyl-cis-3-(trans-4-pentylcyclohexyl)-cyclohexane
r-1-butyl-cis-3-(trans-4-heptylcyclohexyl)-cyclohexane
r-1-propyl-cis-3-(trans-4-ethylcyclohexyl)-cyclohexane
r-1-propyl-cis-3-(trans-4-propylcyclohexyl)-cyclohexane
r-1-propyl-cis-3-(trans-4-butylcyclohexyl)-cyclohexane
r-1-propyl-cis-3-(trans-4-pentylcyclohexyl)-cyclohexane
r-1-propyl-cis-3-(trans-4-heptylcyclohexyl)-cyclohexane
r-1-ethyl-cis-3-(trans-4-ethylcyclohexyl)-cyclohexane
r-1-ethyl-cis-3-(trans-4-propylcyclohexyl)-cyclohexane
r-1-ethyl-cis-3-(trans-4-butylcyclohexyl)-cyclohexane
r-1-ethyl-cis-3-(trans-4-pentylcyclohexyl)-cyclohexane
r-1-ethyl-cis-3-(trans-4-heptylcyclohexyl)-cyclohexane

EXAMPLE 8

50 g of phosphorus oxychloride are added dropwise at 40° to a solution of 10.0 g of cis-3-(trans-4-n-pentylcyclohexyl)-cyclohexanecarboxamide pentylcyclohexyl)-cyclohexanecarboxamide [obtainable by reacting the Grignard compound obtained from 3-(trans-4-n-pentylcyclohexyl)-1-bromocyclohexane (obtained from the corresponding alcohol from Example 3) with $CO_2$ and converting the cyclohexanecarboxylic acid into the amide] in 180 ml of DMF. The reaction mixture is stirred for a further 30 minutes at 50° and, after being cooled to room temperature, is poured onto ice. Working up in the customary manner gives cis-3-(trans-4-n-pentylcyclohexyl)-cyclohexanecarbonitrile.

The following are prepared analogously:
3-(trans-4-heptylcyclohexyl)-cyclohexanecarbonitrile
3-(trans-4-hexylcyclohexyl)-cyclohexanecarbonitrile
3-(trans-4-butylcyclohexyl)-cyclohexanecarbonitrile
3-(trans-4-propylcyclohexyl)-cyclohexanecarbonitrile
3-(trans-4-ethylcyclohexyl)-cyclohexanecarbonitrile 3-[trans-4-(trans-4-heptylcyclohexyl)-cyclohexyl]-cyclohexanecarbonitrile
3-[trans-4-(trans-4-hexylcyclohexyl)-cyclohexyl]-cyclohexanecarbonitrile
3-[trans-4-(trans-4-pentylcyclohexyl)-cyclohexyl]-cyclohexanecarbonitrile
3-[trans-4-(trans-4-propylcyclohexyl)-cyclohexyl]-cyclohexanecarbonitrile
3-[trans-4-(trans-4-ethylcyclohexyl)-cyclohexyl]-cyclohexanecarbonitrile

EXAMPLE 9

62.5 ml of butyllithium in hexane (1.6 m) and 30.2 g of 3-(trans-4-n-pentylcyclohexyl)-cyclohexanecarbonitrile (Example 8), dissolved in 40 ml of toluene, are added successively, at −10° and under an atmosphere of nitrogen, to a solution of 10.1 g of diisopropylamine in 70 ml of THF, and the mixture is stirred for 20 minutes. 14.2 g of methyl iodide are then added at −10° and the mixture is stirred for a further 20 minutes at room temperature. Working up in the customary manner gives r-1-cyano-1-methyl-cis-3-(trans-4-n-pentylcyclohexyl)-cyclohexane.

The following are prepared analogously:
r-1-cyano-1-methyl-cis-3(trans-4-heptylcyclohexyl)cyclohexane
r-1-cyano-1-methyl-cis-3(trans-4-hexylcyclohexyl)cyclohexane
r-1-cyano-1-methyl-cis-3(trans-4-butylcyclohexyl)cyclohexane
r-1-cyano-1-methyl-cis-3(trans-4-propylcyclohexyl)cyclohexane
r-1-cyano-1-methyl-cis-3(trans-4-ethylcyclohexyl)cyclohexane
r-1-cyano-1-methyl-cis-3-[trans-4-(trans-4-heptylcyclohexyl)-cyclohexyl]-cyclohexane
r-1-cyano-1-methyl-cis-3-[trans-4-(trans-4-hexylcyclohexyl)-cyclohexyl]-cyclohexane
r-1-cyano-1-methyl-cis-3-[trans-4-(trans-4-pentylcyclohexyl)-cyclohexyl]-cyclohexane
r-1-cyano-1-methyl-cis-3-[trans-4-(trans-4-butylcyclohexyl)-cyclohexyl]-cyclohexane
r-1-cyano-1-methyl-cis-3-[trans-4-(trans-4-propylcyclohexyl)-cyclohexyl]-cyclohexane
r-1-cyano-1-methyl-cis-3-[trans-4-(trans-4-ethylcyclohexyl)-cyclohexyl]-cyclohexane The following are obtained analogously by alkylation with appropriate alkyl halides:
1-cyano-1-ethyl-3-[trans-4-(trans-4-heptylcyclohexyl)-cyclohexyl]-cyclohexane
1-cyano-1-ethyl-3-[trans-4-(trans-4-hexylcyclohexyl)cyclohexyl]-cyclohexane
1-cyano-1-ethyl-3-[trans-4-(trans-4-pentylcyclohexyl)-cyclohexyl]-cyclohexane
1-cyano-1-ethyl-3-[trans-4-(trans-4-butylcyclohexyl)cyclohexyl]-cyclohexane
1-cyano-1-ethyl-3-[trans-4-(trans-4-propylcyclohexyl)-cyclohexyl]-cyclohexane
1-cyano-1-ethyl-3-[trans-4-(trans-4-ethylcyclohexyl)cyclohexyl]-cyclohexane
1-cyano-1-propyl-3-[trans-4-(trans-4-heptylcyclohexyl)-cyclohexyl]-cyclohexane
1-cyano-1-propyl-3-[trans-4-(trans-4-hexylcyclohexyl)-cyclohexyl]-cyclohexane
1-cyano-1-propyl-3-[trans-4-(trans-4-pentylcyclohexyl)-cyclohexyl]-cyclohexane
1-cyano-1-propyl-3-[trans-4-(trans-4-butylcyclohexyl)-cyclohexyl]-cyclohexane
1-cyano-1-propyl-3-[trans-4-(trans-4-propylcyclohexyl)cyclohexyl]-cyclohexane
1-cyano-1-propyl-3-[trans-4-(trans-4-ethylcyclohexyl)-cyclohexyl]-cyclohexane
1-cyano-1-butyl-3-[trans-4-(trans-4-heptylcyclohexyl)-cyclohexyl]-cyclohexane
1-cyano-1-butyl-3-[trans-4-(trans-4-hexylcyclohexyl)cyclohexyl]-cyclohexane
1-cyano-1-butyl-3-[trans-4-(trans-4-pentylcyclohexyl)-cyclohexyl]-cyclohexane
1-cyano-1-butyl-3-[trans-4-(trans-4-butylcyclohexyl)cyclohexyl]-cyclohexane
1-cyano-1-butyl-3-[trans-4-(trans-4-propylcyclohexyl)-cyclohexyl]-cyclohexane
1-cyano-1-butyl-3-[trans-4-(trans-4-ethylcyclohexyl)cyclohexyl]-cyclohexane
1-cyano-1-pentyl-3-[trans-4-(trans-4-heptylcyclohexyl)-cyclohexyl]-cyclohexane
1-cyano-1-pentyl-3-[trans-4-(trans-4-hexylcyclohexyl)-cyclohexyl]-cyclohexane
1-cyano-1-pentyl-3-[trans-4-(trans-4-pentylcyclohexyl)-cyclohexyl]-cyclohexane
1-cyano-1-pentyl-3-[trans-4-(trans-4-butylcyclohexyl)-cyclohexyl]-cyclohexane
1-cyano-1-pentyl-3-[trans-4-(trans-4-propylcyclohexyl)-cyclohexyl]-cyclohexane
1-cyano-1-pentyl-3-[trans-4-(trans-4-ethylcyclohexyl)-cyclohexyl]-cyclohexane
1-cyano-1-heptyl-3-[trans-4-(trans-4-heptylcyclohexyl)-cyclohexyl]-cyclohexane
1-cyano-1-heptyl-3-[trans-4-(trans-4-hexylcyclohexyl)-cyclohexyl]-cyclohexane
1-cyano-1-heptyl-3-[trans-4-pentylcyclohexyl-cyclohexyl]-cyclohexane
1-cyano-1-heptyl-3-[trans-4-(trans-4-butylcyclohexyl)-cyclohexyl-9 -cyclohexane
1-cyano-1-heptyl-3-[trans-4-(trans-4-propylcyclohexyl)-cyclohexyl]-cyclohexane
1-cyano-1-heptyl-3-[trans-4-(trans-4-ethylcyclohexyl)-cyclohexyl]-cyclohexane
1-cyano-1-ethyl-3-(trans-4-heptylcyclohexyl)-cyclohexane
1-cyano-1-ethyl-3-(trans-4-hexylcyclohexyl)-cyclohexane
1-cyano-1-ethyl-3-(trans-4-pentylcyclohexyl)-cyclohexane
1-cyano-1-ethyl-3-(trans-4-butylcyclohexyl)-cyclohexane
1-cyano-1-ethyl-3-(trans-4-propylcyclohexyl)-cyclohexane
1-cyano-1-ethyl-3-(trans-4-ethylcyclohexyl)-cyclohexane
1-cyano-1-propyl-3-(trans-4-heptylcyclohexyl)-cyclohexane
1-cyano-1-propyl-3-(trans-4-hexylcyclohexyl)-cyclohexane
1-cyano-1-propyl-3-(trans-4-pentylcyclohexyl)-cyclohexane
1-cyano-1-propyl-3-(trans-4-butylcyclohexyl)-cyclohexane
1-cyano-1-propyl-3-(trans-4-propylcyclohexyl)-cyclohexane
1-cyano-1-propyl-3-(trans-4-ethylcyclohexyl)-cyclohexane
1-cyano-1-butyl-3-(trans-4-heptylcyclohexyl)-cyclohexane
1-cyano-1-butyl-3-(trans-4-hexylcyclohexyl)-cyclohexane 1-cyano-1-butyl-3-(trans-4-pentylcyclohexyl)-cyclohexane
1-cyano-1-butyl-3-(trans-4-butylcyclohexyl)-cyclohexane
1-cyano-1-butyl-3-(trans-4-propylcyclohexyl)-cyclohexane
1-cyano-1-butyl-3-(trans-4-ethylcyclohexyl)-cyclohexane
1-cyano-1-pentyl-3-(trans-4-heptylcyclohexyl)-cyclohexane
1-cyano-1-pentyl-3-(trans-4-hexylcyclohexyl)-cyclohexane
1-cyano-1-pentyl-3-(trans-4-pentylcyclohexyl)-cyclohexane
1-cyano-1-pentyl-3-(trans-4-butylcyclohexyl)-cyclohexane
1-cyano-1-pentyl-3-(trans-4-propylcyclohexyl)-cyclohexane
1-cyano-1-pentyl-3-(trans-4-ethylcyclohexyl)-cyclohexane
1-cyano-1-heptyl-3-(trans-4-heptylcyclohexyl)-cyclohexane
1-cyano-1-heptyl-3-(trans-4-hexylcyclohexyl)-cyclohexane
1-cyano-1-heptyl-3-(trans-4-pentylcyclohexyl)-cyclohexane
1-cyano-1-heptyl-3-(trans-4-butylcyclohexyl)-cyclohexane
1-cyano-1-heptyl-3-(trans-4-propylcyclohexyl)-cyclohexane
1-cyano-1-heptyl-3-(trans-4-ethylcyclohexyl)-cyclohexane

EXAMPLE 10

A mixture of 1.8 g of trans-4-n-pentylcyclohexanecarbaldehyde, 1.2 g of n-hexane-1,3-diol, 0.1 g of p-toluenesulfonic acid and 20 ml of toluene is boiled under a water separator for three hours, cooled and worked up in the customary manner. This gives r-4-n-propyl-cis-2-(trans-4-n-pentylcyclohexyl)-1,3-dioxane.

The following are obtained analogously to Example 10 from the corresponding aldehydes and the corresponding 1,3-diols:

4-methyl-2-(trans-4-pentylcyclohexyl)-1,3-dioxane
4-ethyl-2-(trans-4-pentylcyclohexyl)-1,3-dioxane
4-butyl-2-(trans-4-pentylcyclohexyl)-1,3-dioxane
4-pentyl-2-(trans-4-pentylcyclohexyl)-1,3-dioxane
4-heptyl-2-(trans-4-pentylcyclohexyl)-1,3-dioxane
4-methyl-2-(trans-4-propylcyclohexyl)-1,3-dioxane
4-ethyl-2-(trans-4-propylcyclohexyl)-1,3-dioxane
4-propyl-2-(trans-4-propylcyclohexyl)-1,3-dioxane
4-butyl-2-(trans-4-propylcyclohexyl)-1,3-dioxane
4-pentyl-2-(trans-4-propylcyclohexyl)-1,3-dioxane
4-heptyl-2-(trans-4-propylcyclohexyl)-1,3-dioxane
4-methyl-2-(p-ethylphenyl)-1,3-dioxane
4-ethyl-2-(p-ethylphenyl)-1,3-dioxane
4-propyl-2-(p-ethylphenyl)-1,3-dioxane
4-butyl-2-(p-ethylphenyl)-1,3-dioxane
4-pentyl-2-(p-ethylphenyl)-1,3-dioxane
4-heptyl-2-(p-ethylphenyl)-1,3-dioxane
4-methyl-2-(p-propylphenyl)-1,3-dioxane
4-ethyl-2-(p-propylphenyl)-1,3-dioxane
4-propyl-2-(p-propylphenyl)-1,3-dioxane
4-butyl-2-(p-propylphenyl)-1,3-dioxane
4-pentyl-2-(p-propylphenyl)-1,3-dioxane
4-heptyl-2-(p-propylphenyl)-1,3-dioxane
4-methyl-2-(p-butylphenyl)-1,3-dioxane
4-ethyl-2-(p-butylphenyl)-1,3-dioxane
4-propyl-2-(p-butylphenyl)-1,3-dioxane
4-butyl-2-(p-butylphenyl)-1,3-dioxane
4-pentyl-2-(p-butylphenyl)-1,3-dioxane
4-heptyl-2-(p-butylphenyl)-1,3-dioxane
4-methyl-2-(p-pentylphenyl)-1,3-dioxane
4-ethyl-2-(p-pentylphenyl)-1,3-dioxane
4-propyl-2-(p-pentylphenyl)-1,3-dioxane
4-butyl-2-(p-pentylphenyl)-1,3-dioxane
4-pentyl-2-(p-pentylphenyl)-1,3-dioxane
4-heptyl-2-(p-pentylphenyl)-1,3-dioxane
4-methyl-2-(p-methoxyphenyl)-1,3-dioxane
4-ethyl-2-(p-methoxyphenyl)-1,3-dioxane
4-propyl-2-(p-methoxyphenyl)-1,3-dioxane
4-butyl-2-(p-methoxyphenyl)-1,3-dioxane
4-pentyl-2-(p-methoxyphenyl)-1,3-dioxane
4-heptyl-2-(p-methoxyphenyl)-1,3-dioxane
4-methyl-2-(p-ethoxyphenyl)-1,3-dioxane
4-ethyl-2-(p-ethoxyphenyl)-1,3-dioxane
4-propyl-2-(p-ethoxyphenyl)-1,3-dioxane
4-butyl-2-(p-ethoxyphenyl)-1,3-dioxane
4-pentyl-2-(p-ethoxyphenyl)-1,3-dioxane
4-heptyl-2-(p-ethoxyphenyl)-1,3-dioxane
4-methyl-2-(p-butoxyphenyl)-1,3-dioxane
4-ethyl-2-(p-butoxyphenyl)-1,3-dioxane
4-propyl-2-(p-butoxyphenyl)-1,3-dioxane
4-butyl-2-(p-butoxyphenyl)-1,3-dioxane
4-pentyl-2-(p-butoxyphenyl)-1,3-dioxane
4-heptyl-2-(p-butoxyphenyl)-1,3-dioxane
4-methyl-2-(p-cyanophenyl)-1,3-dioxane
4-ethyl-2-(p-cyanophenyl)-1,3-dioxane
4-propyl-2-(p-cyanophenyl)-1,3-dioxane
4-butyl-2-(p-cyanophenyl)-1,3-dioxane
4-pentyl-2-(p-cyanophenyl)-1,3-dioxane
4-heptyl-2-(p-cyanophenyl)-1,3-dioxane
4-methyl-2-(4 1-cyano-3-fluorophenyl)-1,3-dioxane
4-ethyl-2-(4-cyano-3-fluorophenyl)-1,3-dioxane
4-propyl-2-(4-cyano-3-fluorophenyl)-1,3-dioxane
4-butyl-2-(4-cyano-3-fluorophenyl)-1,3-dioxane
4-pentyl-2-(4-cyano-3-fluorophenyl)-1,3-dioxane
4-heptyl-2-(4-cyano-3-fluorophenyl)-1,3-dioxane

EXAMPLE 11

Hydrogenation of 3-(trans-4-n-propylcyclohexyl)-6-n-pentylcyclohex-2-enone [obtainable by the method of P. Place et al., Tetrahedron 34, 1931 (1978) by reacting 2-acetylbutyrolactone with an n-pentyl halide/-NaH, followed by reaction with hydrogen bromide to give 3-acetyl-1-bromo-n-octane, converting the product into the corresponding ethylene ketal, reacting the corresponding Grignard compound with trans-4-n-propylcyclohexanecarbonitrile and a subsequent aldol condensation]analogously to Example 1 gives 2-n-pentyl-5-(trans-4-n-propylcyclohexyl)-cyclohexanone.

EXAMPLE 12

30 ml of DMF and 250 mg of a 60% NaH suspension are added to a solution in 20 ml of benzene of 1.03 g of methyl 4-[trans-4-(trans-4-n-propylcyclohexyl)cyclohexyl]-2-oxocyclohexanecarboxylate (Example 2), and the mixture is stirred under an atmosphere of nitrogen for one hour at room temperature. 0.43 ml of methyl iodide is added and the mixture is stirred for a further 20 hours and worked up in the customary manner. This gives a mixture of stereoisomers (79:21, the isomer having an axial methyl group predominating). Separation by chromatography gives methyl trans-4-[trans-4-(trans-4-n-propylcyclohexyl)cyclohexyl]-2- oxo-1-methylcyclohexane-r-1-carboxylate (m.p. 115°, c.p. 142°) and methyl cis-4-[trans-4 (trans-4-n-propylcyclohexyl)-cyclohexyl]-2-oxo-1-methylcyclohexane r-1-carboxylate (m.p. 107°, c.p. 116°).

The following are prepared analogously: ethyl trans-4-[trans-4-(trans-4-propylcyclohexyl)-cyclohexyl]-2-oxo-1-methylcyclohexane-r-1-carboxylate, m.p. 95°, c.p. 129° propyl trans-4-[trans-4-(trans-4-propylcyclohexyl)-cyclohexyl]-2-oxo-1-methylcyclohexane-r-1-carboxylate butyl trans-4-[trans-4-(trans-4-propylcyclohexyl)-cyclohexyl]-2-oxo-1-methylcyclohexane-r-1-carboxylate pentyl trans-4-[trans-4-(trans-4-propylcyclohexyl)-cyclohexyl]-2-oxo-1-methylcyclohexane-r-1-carboxylate hexyl trans-4-[trans-4-(trans-4-propylcyclohexyl)-cyclohexyl]-2-oxo-1-methylcyclohexane-r-1-carboxylate heptyl trans-4-[trans-4-(trans-4-propylcyclohexyl)-cycloheptyl trans-4-[trans-4-(trans-4-propylcyclohexyl)-cyclohexyl]-2-oxo-1-methylcyclohexane-r-1-carboxylate methyl trans-4-[trans-4-(trans-4-ethylcyclohexyl)-cyclohexyl]-2-oxo-1-methylcyclohexane-r-1-carboxylate ethyl trans-4-[trans-4-(trans-4-ethylcyclohexyl)-cyclohexyl]-2-oxo-1-methylcyclohexane-r-1-carboxylate propyl trans-4-[trans-4-(trans-4-ethylcyclohexyl)-cyclohexyl]-2-oxo-1-methylcyclohexane-r-1-carboxylate butyl trans-4-[trans-4-(trans-4-ethylcyclohexyl)-cyclohexyl]-2-oxo-1-methylcyclohexane-r-1-carboxylate pentyl trans-4-[trans-4-(trans-4-ethylcyclohexyl)-cyclohexyl]-2-oxo-1-methylcyclohexane-r-1-carboxylate heptyl trans-4-[trans-4-(trans-4-ethylcyclohexyl)-cyclohexyl]-2-oxo-1-methylcyclohexane-r-1-carboxylate methyl trans-4-[trans-4-(trans-4-butylcyclohexyl)-cyclohexyl]-2-oxo-1-methylcyclohexane-r-1-carboxylate ethyl trans-4-[trans-4-(trans-4-butylcyclohexyl)-cyclohexyl]-2-oxo-1-methylcyclohexane-r-1-carboxylate propyl trans-4-[trans-4-(trans-4-butylcyclohexyl)-cyclohexyl]-2-oxo-1-methylcyclohexane-r-1-carboxylate butyl trans-4-[trans-4-(trans-4-butylcyclohexyl)-cyclohexyl]-2-oxo-1-methylcyclohexane-r-1-carboxylate pentyl trans-4-[trans-4-(trans-4-butylcyclohexyl)-cyclohexyl]-2-oxo-1-methylcyclohexane-r-1-carboxylate heptyl trans-4-[trans-4-(trans-4-butylcyclohexyl)-cyclohexyl]-2-oxo-1-methylcyclohexane-r-1-carboxylate methyl trans-4-[trans-4-(trans-4-pentylcyclohexyl)-cyclohexyl]-2-oxo-1-methylcyclohexane-r-1-carboxylate ethyl trans-4-[trans-4-(trans-4-pentylcyclohexyl)-cyclohexyl]-2-oxo-1-methylcyclohexane-r-1-carboxylate propyl trans-4-[trans-4-(trans-4-pentylcyclohexyl)-cyclohexyl]-2-oxo-1-methylcyclohexane-r-1-carboxylate butyl trans-4-[trans-4-(trans-4-pentylcyclohexyl)-cyclohexyl]-2-oxo-1-methylcyclohexane-r-1-carboxylate pentyl trans-4-[trans-4-(trans-4-pentylcyclohexyl)-cyclohexyl]-2-oxo-1-methylcyclohexane-r-1-carboxylate heptyl trans-4-[trans-4-(trans-4-pentylcyclohexyl)-cyclohexyl] -2-oxo-1-methylcyclohexane-r-1-carboxylate methyl trans-4-[trans-4-(trans-4-heptylcyclohexyl)-cyclohexyl]-2-oxo-1-methylcyclohexane-r-1-carboxylate ethyl trans-4-[trans-4-(trans-4-heptylcyclohexyl)-cyclohexyl]-2-oxo-1-methylcyclohexane-r-1-carboxylate propyl trans-4-[trans-4-(trans-4-heptylcyclohexyl)-cyclohexyl]-2-oxo-1-methylcyclohexane-r-1-carboxylate butyl trans-4-[trans-4-(trans-4-heptylcyclohexyl)-cyclohexyl]-2-oxo-1-methylcyclohexane-r-1-carboxylate pentyl trans-4-[trans-4-(trans-4-heptylcyclohexyl)-cyclohexyl]-2-oxo-1-methylcyclohexane-r-1-carboxylate heptyl trans-4-[trans-4-(trans-4-heptylcyclohexyl)-cyclohexyl]-2-oxo-1-methylcyclohexane-r-1-carboxylate ethyl cis-4-[trans-4-(trans-4-propylcyclohexyl)-cyclohexyl]-2-oxo-1-methylcyclohexane-r-1-carboxylate, m.p. 85°, c.p. 92° propyl cis-4-[trans-4-(trans-4-propylcyclohexyl)-cyclohexyl]-2-oxo-1-methylcyclohexane-r-1-carboxylate butyl cis-4-[trans-4-(trans-4-propylcyclohexyl)-cyclohexyl]-2-oxo-1-methylcyclohexane-r-1-carboxylate pentyl cis-4-[trans-4-(trans-4-propylcyclohexyl)-cyclohexyl]-2-oxo-1-methylcyclohexane-r-1-carboxylate hexyl cis-4-[trans-4-(trans-4-propylcyclohexyl)-cyclohexyl]-2-oxo-1-methylcyclohexane-r-1-carboxylate heptyl cis-4-[trans-4-(trans-4-propylcyclohexyl)-cyclohexyl]-2-oxo-1-methylcyclohexane-r-1-carboxylate methyl cis-4-[trans-4-(trans-4-ethylcyclohexyl)-cyclohexyl]-2-oxo-1-methylcyclohexane-r-1-carboxylate ethyl cis-4-[trans-4-(trans-4-ethylcyclohexyl)-cyclohexyl]-2-oxo-1-methylcyclohexane-r-1-carboxylate propyl cis-4-[trans-4-(trans-4-ethylcyclohexyl)-cyclohexyl]-2-oxo-1-methylcyclohexane-r-1-carboxylate butyl cis-4-[trans-4-(trans-4-ethylcyclohexyl)-cyclohexyl]-2-oxo-1-methylcyclohexane-r-1-carboxylate pentyl cis-4-[trans-4-(trans-4-ethylcyclohexyl)-cyclohexyl]-2-oxo-1-methylcyclohexane-r-1-carboxylate heptyl cis-4-[trans-4-(trans-4-ethylcyclohexyl)-cyclohexyl]-2-oxo-1-methylcyclohexane-r-1-carboxylate methyl cis-4-[trans-4-(trans-4-butylcyclohexyl)-cyclohexyl]-2-oxo-1-methylcyclohexane-r-1-carboxylate ethyl cis-4-[trans-4-(trans-4-butylcyclohexyl)-cyclohexyl]-2-oxo-1-methylcyclohexane-r-1-carboxylate propyl cis-4-[trans-4-(trans-4-butylcyclohexyl)-cyclohexyl]-2-oxo-1-methylcyclohexane-r-1-carboxylate
butyl cis-4-[trans-4-(trans-4-butylcyclohexyl)-cyclohexyl]-2-oxo-1-methylcyclohexane-r-1-carboxylate
pentyl cis-4-[trans-4-(trans-4-butylcyclohexyl)-cyclohexyl]-2-oxo-1-methylcyclohexane-r-1-carboxylate
heptyl cis-4-[trans-4-(trans-4-butylcyclohexyl)-cyclohexyl]-2-oxo-1-methylcyclohexane-r-1-carboxylate
methyl cis-4-[trans-4-(trans-4-pentylcyclohexyl)-cyclohexyl]-2-oxo-1-methylcyclohexane-r-1-carboxylate
ethyl cis-4-[trans-4-(trans-4-pentylcyclohexyl)-cyclohexyl]-2-oxo-1-methylcyclohexane-r-1-carboxylate
propyl cis-4-[trans-4-(trans-4-pentylcyclohexyl)-cyclohexyl]-2-oxo-1-methylcyclohexane-r-1-carboxylate
butyl cis-4-[trans-4-(trans-4-pentylcyclohexyl)-cyclohexyl]-2-oxo-1-methylcyclohexane-r-1-carboxylate
pentyl cis-4-[trans-4-(trans-4-pentylcyclohexyl)-cyclohexyl]-2-oxo-1-methylcyclohexane-r-1-carboxylate
heptyl cis-4-[trans-4-(trans-4-pentylcyclohexyl)-cyclohexyl]-2-oxo-1-methylcyclohexane-r-1-carboxylate
methyl cis-4-[trans-4-(trans-4-heptylcyclohexyl)-cyclohexyl]-2-oxo-1-methylcyclohexane-r-1-carboxylate
ethyl cis-4-[trans-4-(trans-4-heptylcyclohexyl)-cyclohexyl]-2-oxo-1-methylcyclohexane-r-1-carboxylate
propyl cis-4-[trans-4-(trans-4-heptylcyclohexyl)-cyclohexyl]-2-oxo-1-methylcyclohexane-r-1-carboxylate
butyl cis-4-[trans-4-(trans-4-heptylcyclohexyl)-cyclohexyl]-2-oxo-1-methylcyclohexane-r-1-carboxylate
pentyl cis-4-[trans-4-(trans-4-heptylcyclohexyl)-cyclohexyl]-2-oxo-1-methylcyclohexane-r-1-carboxylate
heptyl cis-4-[trans-4-(trans-4-heptylcyclohexyl)-cyclohexyl]-2-oxo-1-methylcyclohexane-r-1-carboxylate

EXAMPLE 13

8.5 mg of a 60% NaH suspension are added to a solution in 10 ml of dimethoxyethane of 50 mg of methyl 4-[trans-4-(trans-4-n-propylcyclohexyl)-cyclohexyl]-2-oxo-cyclohexanecarboxylate (Example 2), and the mixture is stirred under an atmosphere of nitrogen for 30 minutes at room temperature. A few drops of acetyl chloride are added and the mixture is stirred for a further hour at room temperature and worked up in the customary manner. This gives 1-methoxycarbonyl-4-[trans-4-(trans-4-n-propylcyclohexyl)-cyclohexyl]-1-cyclohexen-2-ol acetate, m.p. 53°, c.p. 113°.

The following are prepared analogously:
1-ethoxycarbonyl-4-[trans-4-(trans-4-propylcyclohexyl)-cyclohexyl]-1-cyclohexen-2-ol acetate
1-propoxycarbonyl-4-[trans-4-(trans-4-propylcyclohexyl)-cyclohexyl]-1-cyclohexen-2-ol acetate
1-butoxycarbonyl-4-[trans-4-(trans-4-propylcyclohexyl)-cyclohexyl]-1-cyclohexen-2-ol acetate
1-pentoxycarbonyl-4-[trans-4-(trans-4-propylcyclohexyl)-cyclohexyl]-1-cyclohexen-2-ol acetate

EXAMPLE 14

52.9 mmol of butyllithium are added at 0° to a mixture of 5.35 g of diisopropylamine and 45 ml of ether, and the mixture is stirred for 45 minutes. After it has been cooled to −85°, a solution of 8.28 g of trans,trans-4-acetyl-4'-n-propylbicyclohexane (m.p. 38°, c.p. 51°, synthesis described in German Offenlegungsschrift No. 3,332,690) in 120 ml of ether is added dropwise and the mixture is stirred at this temperature for 2 hours. A solution of 7.8 g of 1-(trimethylsilyl)-vinyl methyl ketone in 70 ml of ether is then added dropwise at −95°, and, after being stirred for 30 minutes, the mixture is allowed to warm up to room temperature. 80 ml of 10% methanolic KOH solution are added and the mixture is stirred for one hour at room temperature, neutralized with dilute hydrochloric acid and worked up in the customary manner. Purification by chromatography (silica gel; 5:3.5:1.5 petroleum ether:methylene chloride:ether) gives 3-[trans-4-(trans-4-n-propylcyclohexyl)-cyclohexyl]-cyclohex-2-enone, m.p. 96°, c.p. 92° (monotropic).

The following are prepared analogously:
3-[trans-4-(trans-4-ethylcyclohexyl)-cyclohexyl]-cyclohex-2-enone
3-[trans-4-(trans-4-butylcyclohexyl)-cyclohexyl]-cyclohex-2-enone
3-[trans-4-(trans-4-pentylcyclohexyl)-cyclohexyl]-cyclohex-2-enone
3-[trans-4-(trans-4-hexylcyclohexyl)-cyclohexyl]-cyclohex-2-enone
3-[trans-4-(trans-4-heptylcyclohexyl)-cyclohexyl]-cyclohex-2-enone
3-(trans-4-ethylcyclohexyl)-cyclohex-2-enone
3-(trans-4-propylcyclohexyl)-cyclohex-2-enone
3-(trans-4-butylcyclohexyl)-cyclohex-2-enone
3-(trans-4-pentylcyclohexyl)-cyclohex-2-enone
3-(trans-4-hexylcyclohexyl)-cyclohex-2-enone
3-(trans-4-heptylcyclohexyl)-cyclohex-2-enone
3-(trans-4-methoxycyclohexyl)-cyclohex-2-enone
3-(trans-4-ethoxycyclohexyl)-cyclohex-2-enone
3-(trans-4-propoxycyclohexyl)-cyclohex-2-enone
3-(trans-4-butoxycyclohexyl)-cyclohex-2-enone
3-(trans-4-pentoxycyclohexyl)-cyclohex-2-enone

EXAMPLE 15

A mixture of 30 g of (+)-3-methylcyclohexanone, 28 g of morpholine, 0.1 g of p-toluenesulphonic acid and 50 ml of toluene is boiled under a water separator. After the separation of water is ended, the solvent is distilled off together with excess morpholine and the residue is subjected to a vacuum distillation. 27.1 g of 4'-pentylbiphenyhl-4-yl-acetyl chloride in 20 ml of toluene are added to a solution of 13.6 g of the enamine obtained and 9.1 g of triethylamine in 100 ml of toluene. After boiling for 16 hours under reflux, the mixture is hydrolysed and worked up in the customary manner. The oily crude product is subjected to a separation by chromatography (silica gel/toluene) and recrystallized from ethanol. This gives 2-(4'-pentylbiphenyl-4-yl-acetyl)-5-methylcyclohexanone, m.p. 78° (optically active).

The following are prepared analogously:
2-(4'-hexylbiphenyl-4-yl-acetyl)-5-methylcyclohexanone
2-(4'-hexylbiphenyl-4-yl-acetyl)-5-ethylcyclohexanone 2-(4'-hexylbiphenyl-4-yl-acetyl)-5-propylcyclohexanone
2-(4'-hexylbiphenyl-4-yl-acetyl)-5-pentylcyclohexanone
2-(4'-hexylbiphenyl-4-yl-acetyl)-5-heptylcyclohexanone
2-(4'-octylbiphenyl-4-yl-acetyl)-5-methylcyclohexanone
2-(4'-octylbiphenyl-4-yl-acetyl)-5-ethylcyclohexanone
2-(4'-octylbiphenyl-4-yl-acetyl)-5-propylcyclohexanone
2-(4'-octylbiphenyl-4-yl-acetyl)-5-pentylcyclohexanone
2-(4'-octylbiphenyl-4-yl-acetyl)-5-heptylcyclohexanone
2-(4'-methoxybiphenyl-4-yl-acetyl)-5-methylcyclohexanone
2-(4'-methoxybiphenyl-4-yl-acetyl)-5-ethylcyclohexanone
2-(4'-methoxybiphenyl-4-yl-acetyl)-5-propylcyclohexanone
2-(4'-methoxybiphenyl-4-yl-acetyl)-5-pentylcyclohexanone
2-(4'-methoxybiphenyl-4-yl-acetyl)-5-heptylcyclohexanone
2-(4'-ethoxybiphenyl-4-yl-acetyl)-5-methylcyclohexanone
2-(4'-ethoxybiphenyl-4-yl-acetyl)-5-ethylcyclohexanone
2-(4'-ethoxybiphenyl-4-yl-acetyl)-5-propylcyclohexanone
2-(4'-ethoxybiphenyl-4-yl-acetyl)-5-pentylcyclohexanone
2-(4'-ethoxybiphenyl-4-yl-acetyl)-5-heptylcyclohexanone
2-(4'-propoxybiphenyl-4-yl-acetyl)-5-methylcyclohexanone
2-(4'-propoxybiphenyl-4-yl-acetyl)-5-ethylcyclohexanone
2-(4'-propoxybiphenyl-4-yl-acetyl)-5-propylcycohexanone
2-(4'-propoxybiphenyl-4-yl-acetyl)-5-pentylcyclohexanone
2-(4'-propoxybiphenyl-4-yl-acetyl)-5-heptylcyclohexanone
2-(4'-butoxybiphenyl-4-yl-acetyl)-5-methylcyclohexanone
2-(4'-butoxybiphenyl-4-yl-acetyl)-5-ethylcyclohexanone
2-(4'-butoxybiphenyl-4-yl-acetyl)-5-propylcyclohexanone
2-(4'-butoxybiphenyl-4-yl-acetyl)-5-pentylcyclohexanone
2-(4'-butoxybiphenyl-4-yl-acetyl)-5-heptylcyclohexanone
2-(4'-pentoxybiphenyl-4-yl-acetyl)-5-methylcyclohexanone
2-(4'-pentoxybiphenyl-4-yl-acetyl)-5-ethylcyclohexanone
2-(4'-pentoxybiphenyl-4-yl-acetyl)-5-propylcyclohexanone
2-(4'-pentoxybiphenyl-4-yl-acetyl)-5-pentylcyclohexanone
2-(4'-pentoxybiphenyl-4-yl-acetyl)-5-heptylcyclohexanone
2-(4'-hexoxybiphenyl-4-yl-acetyl)-5-methylcyclohexanone
2-(4'-hexoxybiphenyl-4-yl-acetyl)-5-ethylcyclohexanone
2-(4'-hexoxybiphenyl-4-yl-acetyl)-5-propylcyclohexanone
2-(4'-hexoxybiphenyl-4-yl-acetyl)-5-pentylcyclohexanone
2-(4'-hexoxybiphenyl-4-yl-acetyl)-5-heptylcyclohexanone
2-(4'-heptoxybiphenyl-4-yl-acetyl)-5-methylcyclohexanone
2-(4'-heptoxybiphenyl-4-yl-acetyl)-5-ethylcyclohexanone
2-(4'-heptoxybiphenyl-4-yl-acetyl)-5-propylcyclohexanone
2-(4'-heptoxybiphenyl-4-yl-acetyl)-5-pentylcyclohexanone
2-(4'-heptoxybiphenyl-4-yl-acetyl)-5-heptylcyclohexanone
2-(4'-octoxybiphenyl-4-yl-acetyl)-5-methylcyclohexanone
2-(4'-octoxybiphenyl-4-yl-acetyl)-5-ethylcyclohexanone
2-(4'-octoxybiphenyl-4-yl-acetyl)-5-propylcyclohexanone
2-(4'-octoxybiphenyl-4-yl-acetyl)-5-pentylcyclohexanone
2-(4'-octoxybiphenyl-4-yl-acetyl)-5-heptylcyclohexanone
2-(4'-nonoxybiphenyl-4-yl-acetyl)-5-methylcyclohexanone
2-(4'-nonoxybiphenyl-4-yl-acetyl)-5-ethylcyclohexanone
2-(4'-nonoxybiphenyl-4-yl-acetyl)-5-propylcyclohexanone
2-(4'-nonoxybiphenyl-4-yl-acetyl)-5-pentylcyclohexanone
2-(4'-nonoxybiphenyl-4-yl-acetyl)-5-heptylcyclohexanone
2-[p-(5-hexylpyrimidine-2-yl)-phenylacetyl]-5-methylcyclohexanone
2-[p-(5-hexylpyrimidine-2-yl)-phenylacetyl]-5-ethylcyclohexanone
2-[p-(5-hexylpyrimidine-2-yl)-phenylacetyl]-5-propylcyclohexanone
2-[p-(5-hexylpyrimidine-2-yl)-phenylacetyl]-5-pentylcyclohexanone
2-[p-(5-hexylpyrimidine-2-yl)-phenylacetyl]-5-heptylcyclohexanone
2-[p-(5-octylpyrimidine-2-yl)-phenylacetyl]-5-methylcyclohexanone
2-[p-(5-octylpyrimidine-2-yl)-phenylacetyl]-5-ethylcyclohexanone
2-[p-(5-octylpyrimidine-2-yl)-phenylacetyl]-5-propylcyclohexanone
2-[p-(5-octylpyrimidine-2-yl)-phenylacetyl]-5-pentylcyclohexanone
2-[p-(5-octylpyrimidine-2-yl)-phenylacetyl]-5-heptylcyclohexanone
b    2-[p-(5-nonylpyrimidine-2-yl)-phenylacetyl]-5-methylcyclohexanone
2-[p-(5-nonylpyrimidine-2-yl)-phenylacetyl]-5-ethylcyclohexanone
2-[p-(5-nonylpyrimidine-2-yl)-phenylacetyl]-5-propylcyclohexanone
2-[p-(5-nonylpyrimidine-2-yl)-phenylacetyl]-5-pentylcyclohexanone
2-[p-(5-nonylpyrimidine-2-yl)-phenylacetyl]-5-heptylcyclohexanone
2-[p-(5-decylpyrimidine-2-yl)-phenylacetyl]-5-methylcyclohexanone
2-[p-(5-decylpyrimidine-2-yl)-phenylacetyl]-5-ethylcyclohexanone 2-[p-(5-decylpyrimidine-2-yl)-phenylacetyl]-5-propylcyclohexanone
2-[p-(5-decylpyrimidine-2-yl)-phenylacetyl]-5-pentylcyclohexanone
2-[p-(5-decylpyrimidine-2-yl)-phenylacetyl]-5-heptylcyclohexanone
2-[p-(5-heptylpyrimidine-2-yl)-phenylacetyl]-5-methylcyclohexanone
2-[p-(5-heptylpyrimidine-2-yl)-phenylacetyl]-5-ethylcyclohexanone
2-[p-(5-heptylpyrimidine-2-yl)-phenylacetyl]-5-propylcyclohexanone
2-[p-(5-heptylpyrimidine-2-yl)-phenylacetyl]-5-pentylcyclohexanone
2-[p-(5-heptylpyrimidine-2-yl)-phenylacetyl]-5-heptylcyclohexanone
2-[p-(5-pentylpyrimidine-2-yl)-phenylacetyl]-5-methylcyclohexanone
2-[p-(5-pentylpyrimidine-2-yl)-phenylacetyl]-5-ethylcyclohexanone
2-[p-(5-pentylpyrimidine-2-yl)-phenylacetyl]-5-propylcyclohexanone
2-[p-(5-pentylpyrimidine-2-yl)-phenylacetyl]-5-pentylcyclohexanone
2-[p-(5-pentylpyrimidine-2-yl)-phenylacetyl]-5-heptylcyclohexanone
2-[p-(5-hexylpyridine-2-yl)-phenylacetyl]-5-methylcyclohexanone
2-[p-(5-hexylpyridine-2-yl)-phenylacetyl]-5-ethylcyclohexanone
2-[p-(5-hexylpyridine-2-yl)-phenylacetyl]-5-propylcyclohexanone
2-[p-(5-hexylpyridine-2-yl)-phenylacetyl]-5-pentylcyclohexanone
2-[p-(5-hexylpyridine-2-yl)-phenylacetyl]-5-heptylcyclohexanone
2-[p-(trans-4-pentylcyclohexyl)-phenylacetyl]-5-methylcyclohexanone
2-[p-(trans-4-pentylcyclohexyl)-phenylacetyl]-5-ethylcyclohexanone
2-[p-(trans-4-pentylcyclohexyl)-phenylacetyl]-5-propylcyclohexanone
2-[p-(trans-4-pentylcyclohexyl)-phenylacetyl]-5-pentylcyclohexanone
2-[p-(trans-4-pentylcyclohexyl)-phenylacetyl]-5-heptylcyclohexanone
2-[p-(trans-4-heptylcyclohexyl)-phenylacetyl]-5-methylcyclohexanone
2-[p-(trans-4-heptylcyclohexyl)-phenylacetyl]-5-ethylcyclohexanone
2-[p-(trans-4-heptylcyclohexyl)-phenylacetyl]-5-propylcyclohexanone
2-[p-(trans-4-heptylcyclohexyl)-phenylacetyl]-5-pentylcyclohexanone
2-[p-(trans-4-heptylcyclohexyl)-phenylacetyl]-5-heptylcyclohexanone
2-[p-(trans-4-propylcyclohexyl)-phenylacetyl]-5-methylcyclohexanone
2-[p-(trans-4-propylcyclohexyl)-phenylacetyl]-5-ethylcyclohexanone
2-[p-(trans-4-propylcyclohexyl)-phenylacetyl]-5-propylcyclohexanone
2-[p-(trans-4-propylcyclohexyl)-phenylacetyl]-5-pentylcyclohexanone
2-[p-(trans-4-propylcyclohexyl)-phenylacetyl]-5-heptylcyclohexanone
2-(trans-trans-4-propylcyclohexylcyclohex-4'-yl-acetyl)-5-methylcyclohexanone
2-(trans-trans-4-propylcyclohexylcyclohex-4'-yl-acetyl)-5-ethylcyclohexanone
2-(trans-trans-4-propylcyclohexylcyclohex-4'-yl-acetyl)-5-propylcyclohexanone
2-(trans-trans-4-propylcyclohexylcyclohex-4'-yl-acetyl)-5-pentylcyclohexanone
2-(trans-trans-4-propylcyclohexylcyclohex-4'-yl-acetyl)-5-heptylcyclohexanone
2-(trans-trans-4-pentylcyclohexylcyclohex-4'-yl-acetyl)-5-methylcyclohexanone
2-(trans-trans-4-pentylcyclohexylcyclohex-4'-yl-acetyl)-5-ethylcyclohexanone
2-(trans-trans-4-pentylcyclohexylcyclohex-4'-yl-acetyl)-5-propylcyclohexanone
2-(trans-trans-4-pentylcyclohexylcyclohex-4'-yl-acetyl)-5-pentylcyclohexanone
2-(trans-trans-4-pentylcyclohexylcyclohex-4'-yl-acetyl)-5-heptylcyclohexanone
2-(trans-trans-4-heptylcyclohexylcyclohex-4'-yl-acetyl)-5-methylcyclohexanone
2-(trans-trans-4-heptylcyclohexylcyclohex-4'-yl-acetyl)-5-ethylcyclohexanone
2-(trans-trans-4-heptylcyclohexylcyclohex-4'-yl-acetyl)-5-propylcyclohexanone
2-(trans-trans-4-heptylcyclohexylcyclohex-4'-yl-acetyl)-5-pentylcyclohexanone
2-(trans-trans-4-heptylcyclohexylcyclohex-4'-yl-acetyl)-5-heptylcyclohexanone
2-[trans-4-(p-ethoxyphenyl)-cyclohexylacetyl]-5-methylcyclohexanone
2-[trans-4-(p-ethoxyphenyl)-cyclohexylacetyl]-5-ethylcyclohexanone
2-[trans-4-(p-ethoxyphenyl)-cyclohexylacetyl]-5-propylcyclohexanone
2-[trans-4-(p-ethoxyphenyl)-cyclohexylacetyl]-5-pentylcyclohexanone
2-[trans-4-(p-ethoxyphenyl)-cyclohexylacetyl]-5-heptylcyclohexanone
2-[trans-4-(p-butoxyphenyl)-cyclohexylacetyl]-5-methylcyclohexanone
2-[trans-4-(p-butoxyphenyl)-cyclohexylacetyl]-5-ethylcyclohexanone
2-[trans-4-(p-butoxyphenyl)-cyclohexylacetyl]-5-propylcyclohexanone
2-[trans-4-(p-butoxyphenyl)-cyclohexylacetyl]-5-pentylcyclohexanone
2-[trans-4-(p-butoxyphenyl)-cyclohexylacetyl]-5-heptylcyclohexanone
2-[trans-4-(p-hexoxyphenyl)-cyclohexylacetyl]-5-methylcyclohexanone
2-[trans-4-(p-hexoxyphenyl)-cyclohexylacetyl]-5-ethylcyclohexanone
2-[trans-4-(p-hexoxyphenyl)-cyclohexylacetyl]-5-propylcyclohexanone
2-[trans-4-(p-hexoxyphenyl)-cyclohexylacetyl]-5-pentylcyclohexanone
2-[trans-4-(p-hexoxyphenyl)-cyclohexylacetyl]-5-heptylcyclohexanone
2-[trans-4-(p-octoxyphenyl)-cyclohexylacetyl]-5-methylcyclohexanone
2-[trans-4-(p-octoxyphenyl)-cyclohexylacetyl]-5-ethylcyclohexanone
2-[trans-4-(p-octoxyphenyl)-cyclohexylacetyl]-5-propylcyclohexanone
2-[trans-4-(p-octoxyphenyl)-cyclohexylacetyl]-5-pentylcyclohexanone
2-[trans-4-(p-octoxyphenyl)-cyclohexylacetyl]-5-heptylcyclohexanone 2-[trans-4-(p-nonoxyphenyl)-cyclohexylacetyl]-5-methylcyclohexanone
2-[trans-4-(p-nonoxyphenyl)-cyclohexylacetyl]-5-ethylcyclohexanone
2-[trans-4-(p-nonoxyphenyl)-cyclohexylacetyl]-5-propylcyclohexanone
2-[trans-4-(p-nonoxyphenyl)-cyclohexylacetyl]-5-pentylcyclohexanone
2-[trans-4-(p-nonoxyphenyl)-cyclohexylacetyl]-5-heptylcyclohexanone
2-(p-ethoxyphenylacetyl)-5-methylcyclohexanone
2-(p-ethoxyphenylacetyl)-5-ethylcyclohexanone
2-(p-ethoxyphenylacetyl)-5-propylcyclohexanone
2-(p-ethoxyphenylacetyl)-5-pentylcyclohexanone
2-(p-ethoxyphenylacetyl)-5-heptylcyclohexanone
2-(p-butoxyphenylacetyl)-5-methylcyclohexanone
2-(p-butoxyphenylacetyl)-5-ethylcyclohexanone
2-(p-butoxyphenylacetyl)-5-propylcyclohexanone
2-(p-butoxyphenylacetyl)-5-pentylcyclohexanone
2-(p-butoxyphenylacetyl)-5-heptylcyclohexanone
2-(p-hexoxyphenylacetyl)-5-methylcyclohexanone
2-(p-hexoxyphenylacetyl)-5-ethylcyclohexanone
2-(p-hexoxyphenylacetyl)-5-propylcyclohexanone
2-(p-hexoxyphenylacetyl)-5-pentylcyclohexanone
2-(p-hexoxyphenylacetyl)-5-heptylcyclohexanone
2-(p-nonoxyphenylacetyl)-5-methylcyclohexanone
2-(p-nonoxyphenylacetyl)-5-ethylcyclohexanone
2-(p-nonoxyphenylacetyl)-5-propylcyclohexanone
2-(p-nonoxyphenylacetyl)-5-pentylcyclohexanone
2-(p-nonoxyphenylacetyl)-5-heptylcyclohexanone

EXAMPLE 16

A solution of lithium diisopropylamide—prepared from 60 ml of THF, 13.2 g of diisopropylamine and 75 ml of a 1.6-molar solution of n-butyllithium in hexane—is added slowly at −78° under a nitrogen atmosphere to a solution of 26.3 g of trans,trans-4'-pentylbicyclohexyl-4-carbonitrile in 100 ml of THF. After stirring for one hour, 11.5 g of 2-cyclohexen-1-one are slowly added dropwise. After stirring for one further hour, the reaction mixture is warmed to room temperature and hydrolysed. After working up in the customary manner, further purification by chromatography (silica gel/toluene) and recrystallizing from acetone, this gives r-1-cyano-1-(3-oxocyclohexyl)-cis-4-(trans-4-pentylcyclohexyl)-cyclohexane, m.p. 120°.

The following are prepared analogously:
r-1-cyano-1-(3-oxo-4-propylcyclohexyl)-cis-4-(trans-4-pentylcyclohexyl)-cyclohexane
r-1-cyano-1-(3-oxocyclohexyl)-cis-4-(p-propylphenyl)-cyclohexane
r-1-cyano-1-(3-oxocyclohexyl)-cis-4-(p-butylphenyl)-cyclohexane
r-1-cyano-1-(3-oxocyclohexyl)-cis-4-(p-pentylphenyl)-cyclohexane
r-1-cyano-1-(3-oxocyclohexyl)-cis-4-(p-heptylphenyl)-cyclohexane
r-1-cyano-1-(3-oxocyclohexyl)-cis-4-(p-octylphenyl)-cyclohexane
r-1-cyano-1-(3-oxocyclohexyl)-cis-4-(p-methoxyphenyl)-cyclohexane
r-1-cyano-1-(3-oxocyclohexyl)-cis-4-(p-butoxyphenyl)-cyclohexane
r-1-cyano-1-(3-oxocyclohexyl)-cis-4-(p-pentoxyphenyl)-cyclohexane
r-1-cyano-1-(3-oxocyclohexyl)-cis-4-(p-hexoxyphenyl)-cyclohexane
r-1-cyano-1-(3-oxocyclohexyl)-cis-4-(4-propylbiphenyl-4'-yl)-cyclohexane
r-1-cyano-1-(3-oxocyclohexyl)-cis-4-(4-butylbiphenyl-4'-yl)-cyclohexane
r-1-cyano-1-(3-oxocyclohexyl)-cis-4-(4-pentylbiphenyl-4'-yl)-cyclohexane
r-1-cyano-1-(3-oxocyclohexyl)-cis-4-(4-heptylbiphenyl-4'-yl)-cyclohexane
r-1-cyano-1-(3-oxocyclohexyl)-cis-4-(4-octylbiphenyl-4'-yl)-cyclohexane
r-1-cyano-1-(3-oxocyclohexyl)-cis-4-(4-methoxybiphenyl-4'-yl)-cyclohexane
r-1-cyano-1-(3-oxocyclohexyl)-cis-4-(4-butoxybiphenyl-4'-yl)-cyclohexane
r-1-cyano-1-(3-oxocyclohexyl)-cis-4-(4-pentoxybiphenyl-4'-yl)-cyclohexane
r-1-cyano-1-(3-oxocyclohexyl)-cis-4-(4-hexoxybiphenyl-4'-yl)-cyclohexane
r-1-cyano-1-(3-oxo-4-propylcyclohexyl)-cis-4-(4-propylbiphenyl-4'-yl)-cyclohexane
r-1-cyano-1-(3-oxo-4-propylcyclohexyl)-cis-4-(4-butylbiphenyl-4'-yl)-cyclohexane
r-1-cyano-1-(3-oxo-4-propylcyclohexyl)-cis-4-(4-pentylbiphenyl-4'-yl)-cyclohexane
r-1-cyano-1-(3-oxo-4-propylcyclohexyl)-cis-4-(4-heptylbiphenyl-4'-yl)-cyclohexane
r-1-cyano-1-(3-oxo-4-propylcyclohexyl)-cis-4-(4-octylbiphenyl-4'-yl)-cyclohexane
r-1-cyano-1-(3-oxo-4-propylcyclohexyl)-cis-4-(4-methoxybiphenyl-4'-yl)-cyclohexane
r-1-cyano-1-(3-oxo-4-propylcyclohexyl)-cis-4-(4-butoxybiphenyl-4'-yl)-cyclohexane
r-1-cyano-1-(3-oxo-4-propylcyclohexyl)-cis-4-(4-pentoxybiphenyl-4'-yl)-cyclohexane
r-1-cyano-1-(3-oxo-4-propylcyclohexyl)-cis-4-(4-hexoxybiphenyl-4'-yl)-cyclohexane The following are examples of liquid-crystal phases containing at least one compound of the formula I:

EXAMPLE A

A liquid-crystal phase consisting of:
17% of p-(trans-4-propylcyclohexyl)-benzonitrile,
22% of p-(trans-4-butylcyclohexyl)-benzonitrile,
24% of p-(trans-4-pentylcyclohexyl)-benzonitrile,
14% of p-(trans-4-heptylcyclohexyl)-benzonitrile,
18% of 4-ethyl-4'-(trans-4-pentylcyclohexyl)-biphenyl and
5% of trans-2-(p-propylphenyl)-5-pentylcyclohexanone
is prepared.

EXAMPLE B

A liquid-crystal phase consisting of:
16% of trans-1-(p-ethoxyphenyl)-4-propylcyclohexane,
12% of trans-1-(p-butoxyphenyl)-4-propylcyclohexane,
16% p-(trans-4-propylcyclohexyl)-benzonitrile,
23% of p-(trans-4-pentylcyclohexyl)-benzonitrile,
15% of p-(trans-4-heptylcyclohexyl)-benzonitrile and
18% of 3-[trans-4-(trans-4-propylcyclohexyl)-cyclohexyl]-cyclohexanone,
is prepared.

EXAMPLE C

A liquid-crystal phase consisting of:
16% trans-1-(p-ethoxyphenyl)-4-propylcyclohexane,
12% of trans-1-(p-butoxyphenyl)-4-propylcyclohexane,
16% of p-(trans-4-propylcyclohexyl)-benzonitrile,
23% of p-(trans-4-pentylcyclohexyl)-benzonitrile,
15% of p-(trans-4-heptylcyclohexyl)-benzonitrile and 18% of r-1-butyryloxy-cis-3-[trans-4-(trans-4-propylcyclohexyl)-cyclohexyl]-cyclohexane
is prepared.

EXAMPLE D

A ferroelectric liquid-crystal phase consisting of:
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
27% of 2-p-nonyloxyphenyl-5-nonylpyrimidine
26% of r-1-cyano-cis-4-(4'-butyloxybiphenyl-4-yl)-1-octylcyclohexane
13% of r-1-cyano-cis-4-(4'-hexylbiphenyl-4-yl)-1-heptylcyclohexane
5% of r-1-cyano-1-(trans-4-pentylcyclohexyl)-cis-4-(trans-4-pentylcyclohexyl)-cyclohexane and
10% of r-1-cyano-1-(3-oxocyclohexyl)-cis-4-(trans-4-pentylcyclohexyl)-cyclohexane (optically active)
shows $K/S_c^* -7°$, $S_c^*/S_A^* 54°$, $S_A^*/Ch 79°$, $Ch/I 90°$.

We claim:

1. A liquid-crystal phase having at least two liquid crystal components, and comprising at least one transversely polarized 1,4-cyclohexylene compound of the formula I $$R^1-A^1-Z^1-A^2-R^2 \quad \text{I}$$

wherein
$R^1$ and $R^2$ are independently H or an alkyl group which has 1-10 C atoms and in which one or two non-adjacent $CH_2$ groups can also be replaced by O atoms and/or $-CO-$ groups and/or $-CO-O-$ groups and/or $-CH=CH-$ groups, or F, Cl, Br, CN or $R^3-A^3-Z^2-$,
$A^1$ is $-A-$, $A^4-Z^0-A-$ or $-A-Z^0-A^4-$,
A is a group of formula (A) or (J):

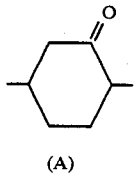 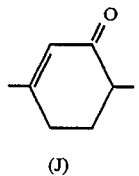

(A)        (J)

or the mirror image thereof,
$A^2$, $A^3$ and $A^4$ are each 1,4-phenylene which is unsubstituted or substituted by one or two F and/or Cl atoms and/or $CH_3$ groups and/or CN groups and in which one or two CH groups can also be replaced by M atoms and/or NO, or are 1,4-cyclohexylene wherein one or two non-adjacent $CH_2$ groups can also be replaced by O atoms, or are 1,3-dithiane-2,5-diyl, piperidine-1,4-diyl, 1,4-bicyclo-[2,2,2] octylene, decahydronaphthalene-2,6-diyl or 1,2,3,4-tetra-hydronaphthalene-2,6-diyl groups or are $-A-$,
$Z^0$, $Z^1$ and $Z^2$ are each $-CO-O-$, $-O-CO-$, $-CH_2CH_2-$, $-OCH_2-$, $-CH_2O-$, $-CH_2CO-$, $-COCH_2-$, $-CH_2CHCN-$, $-CHCNCH_2-$ or a single bond, and
$R^3$ is H or an alkyl group which has 1-10 C atoms and in which one or two non-adjacent $CH_2$ groups can also be replaced by O atoms and/or $-CO-$ groups and/or $-CO-O-$ groups and/or $-CH=CH-$ groups, or is F, Cl, Br or CN.

2. Phase according to claim 1 which contains at least one compound of the partial formulae Ia or Ib (having two rings)

$$R^1-A-A^2-R^2 \quad \text{Ia}$$

$$R^1-A-Z^1-A^2-R^2 \quad \text{Ib}$$

Ic and Ii (having three rings)

$$R^1-A^4-A-A^2-R^2 \quad \text{Ic}$$

$$R^1-A-A^4-A^2-R^2 \quad \text{Id}$$

$$R^1-A^4-A-Z^1-A^2-R^2 \quad \text{Ie}$$

$$R^1-A-A^4-Z^1-A^2-R^2 \quad \text{If}$$

$$R^1-A-Z^1-A^2-A^3-R^3 \quad \text{Ig}$$

$$R^3-A^3-Z^2-A-Z^1-A^2-R^2 \quad \text{Ih}$$

$$R^1-A-Z^1-A^2-Z^2-A^3-R^3 \quad \text{Ii}$$

or Ij to Ip (having four rings)

$$R^1-A^4-A-A^2-A^3-R^3 \quad \text{Ij}$$

$$R^1-A-A^4-A^2-A^3-R^3 \quad \text{Ik}$$

$$R^3-A^3-Z^2-A^4-A-A^2-R^2 \quad \text{Il}$$

$$R^3-A^3-A^4-A-Z^1-A^2-R^2 \quad \text{Im}$$

$$R^1-A-A^4-A^2-Z^2-A^3-R^3 \quad \text{In}$$

$$R^1-A-A^4-Z^1-A^2-A^3-R^3 \quad \text{Io}$$

$$R^1-A^4-A-Z^1-A^2-A^3-R^3 \quad \text{Ip}$$

3. Phase according to claim 1, wherein $R^1$, $R^2$ and $R^3$ are alkyl, alkoxy or oxaalkyl.

4. Phase according to claim 1, wherein one of the radicals $R^1$, $R^2$ and $R^3$ is $-CO$-alkyl, $-O-CO$-alkyl, $-CO-O$-alkyl or CN, and the other is alkyl.

5. Phase according to claim 1, wherein the alkyl radicals, can have a $CH_2$ group replaced by an O atom, are linear and have 2, 3, 4, 5, 6 or 7 C atoms.

6. Phase according to claim 1, wherein $A^2$, $A^3$ and $A^4$ are independently 1,4-cyclohexylene, 1,4-phenylene, 2-fluoro-1,4-phenylene, pyrimidine-2,5-diyl, pyridazine-3,6-diyl, pyridine-2,5-diyl or pyrazine-2,5-diyl.

7. Phase according to claim 6, wherein $A^2$, $A^3$ and $A^4$ are independently 1,4-phenylene or pyrimidine-2,5-diyl.

8. Phase according to claim 1, wherein $Z^1$ and $Z^2$ are $-O-CO-$, $-CO-O-$, $-CH_2CO-$, $-COCH_2-$, $-CH_2CH_2-$ or a single bond.

9. Phase according to claim 8, wherein $Z^1$ and $Z^2$ are single bonds.

10. Phase according to claim 1, wherein $Z^0$ is a single bond.

11. Phase according to claim 1, wherein A is a group of formula (A).

12. Phase according to claim 1 which contains at least compound of the following formulae:

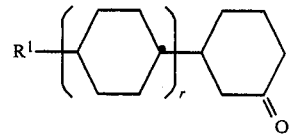

I1

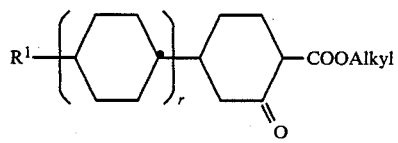

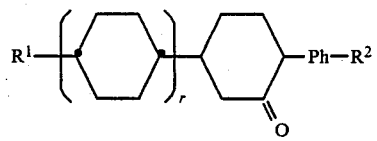

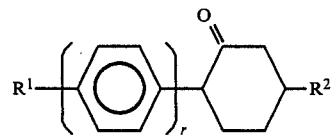

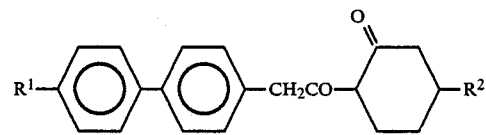

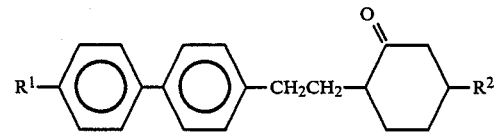

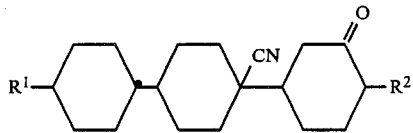

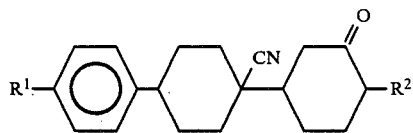

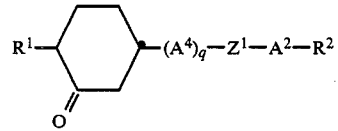

wherein r is 0 or 1.

13. Phase according to claim 1, wherein the substituents $R^1—$, $R^1—A^4—$, $R^2—A^2—Z^1—$ or $R^2—A^2—Z^1—A^4$ in the 1-position and 4-position of the ring A are in the transconfiguration and assume the equatorial position.

14. Phase according to claim 1 which contains at least one cyclophexanone derivative of the formula II $$R^1—\text{[cyclohexanone]}—(A^4)_q—Z^1—A^2—R^2 \quad \text{II}$$

wherein $R^1$ is an alkyl group having 1–10 C atoms, q is 0 or 1 and $A^4$, $Z^1$, $A^2$ and $R^2$ have the meaning indicated in formula I.

15. In a liquid-crystal display device containing a liquid crystal phase, the improvement wherein the phase is one according to claim 1.

16. In an electrooptical display device containing a liquid crystal dielectric, the improvement wherein the dielectric is a phase according to claim 1.

* * * * *